US008931477B2

(12) United States Patent
Ogilvie et al.

(10) Patent No.: US 8,931,477 B2
(45) Date of Patent: Jan. 13, 2015

(54) ADJUSTABLE ORAL AIRWAY DEVICES, AND ADJUSTABLE ORAL AIRWAY KITS

(76) Inventors: Daniel Ogilvie, Spokane, WA (US); Beata Zawadzka, Spokane, WA (US)

(*) Notice: Subject to any disclaimer, the term of this patent is extended or adjusted under 35 U.S.C. 154(b) by 881 days.

(21) Appl. No.: 13/023,873

(22) Filed: Feb. 9, 2011

(65) Prior Publication Data
US 2011/0126840 A1 Jun. 2, 2011

Related U.S. Application Data

(63) Continuation-in-part of application No. 12/409,022, filed on Mar. 23, 2009, now Pat. No. 8,297,275.

(51) Int. Cl.
A61M 16/00 (2006.01)
A62B 9/06 (2006.01)
A61M 16/04 (2006.01)

(52) U.S. Cl.
CPC ....... A61M 16/0488 (2013.01); A61M 16/0493 (2013.01); A61M 16/0495 (2013.01)
USPC ................................ 128/200.26; 128/207.14

(58) Field of Classification Search
CPC .......... A61M 16/0488; A61M 16/049; A61M 16/0497; A61M 16/0493; A61M 16/0495; A61M 2016/0418
USPC .......... 128/859, 860, 200.15, 200.24, 200.26, 128/207.14, 207.17
See application file for complete search history.

(56) References Cited

U.S. PATENT DOCUMENTS

| 2,127,215 | A | * | 8/1938 | Gwathmey ............... 128/207.14 |
| 3,774,616 | A | | 11/1973 | White et al. |
| 3,930,507 | A | | 1/1976 | Berman |
| 4,064,873 | A | * | 12/1977 | Swenson ....................... 600/215 |
| 4,068,658 | A | | 1/1978 | Berman |
| 4,112,936 | A | | 9/1978 | Blachly |
| 4,365,625 | A | | 12/1982 | Rind |
| 4,425,911 | A | * | 1/1984 | Luomanen et al. ...... 128/200.26 |
| 4,919,126 | A | | 4/1990 | Baildon |
| 5,353,787 | A | * | 10/1994 | Price ....................... 128/200.26 |
| 5,421,327 | A | | 6/1995 | Flynn et al. |
| 5,590,643 | A | | 1/1997 | Flam |
| 5,697,890 | A | * | 12/1997 | Kolfenbach et al. .......... 600/235 |
| 5,740,791 | A | | 4/1998 | Aves |
| 6,386,199 | B1 | | 5/2002 | Alfery |
| 8,197,402 | B1 | * | 6/2012 | Cedeno ........................ 600/194 |
| 2008/0058599 | A1 | * | 3/2008 | Schwartz et al. ............. 600/139 |
| 2008/0156324 | A1 | | 7/2008 | Isenberg et al. |

* cited by examiner

Primary Examiner — Lynne Anderson
Assistant Examiner — Bradley Philips
(74) Attorney, Agent, or Firm — Wells St. John P.S.

(57) ABSTRACT

Some embodiments include oral airway assemblies that can include a body having an opening extending from a first end of the body to a second end of the body with the body having upper and lower portions in one cross section. A flange can be included that extends from the first end of the body and outwardly from the opening. An upper member extending from the upper portion of the second end of the body and outwardly from the opening away from the lower portion can be provided. The assemblies can include a lower member slidably engaged with the body, with at least a portion of the lower member extending outwardly from the lower portion of the second end of the body and away from the upper portion when engaged with the body. In accordance with other embodiments a member can be provided to slidably engage with the body, and include a tab at one end, with the tab being pivotably coupled to the member.

8 Claims, 31 Drawing Sheets

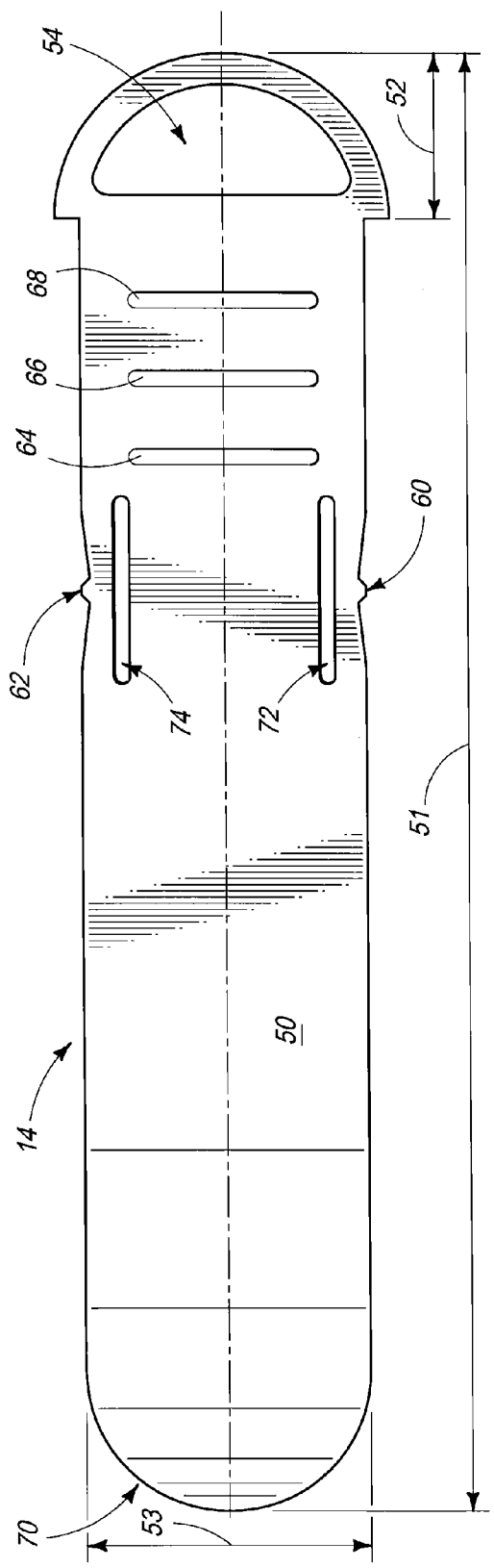
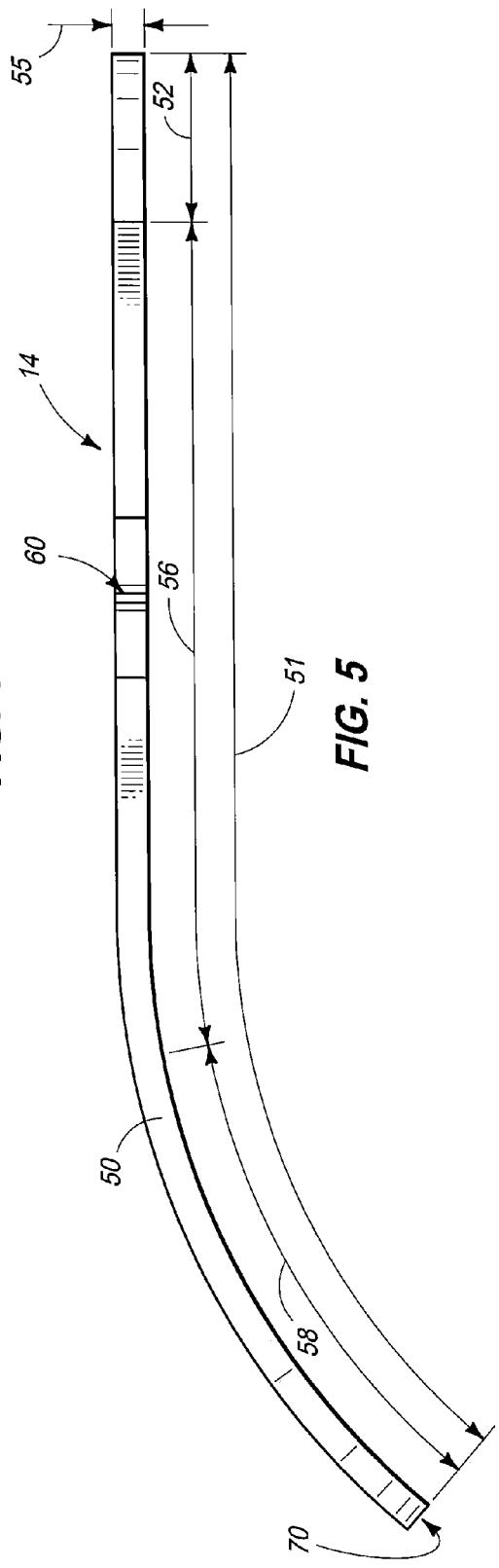
FIG. 4
FIG. 5

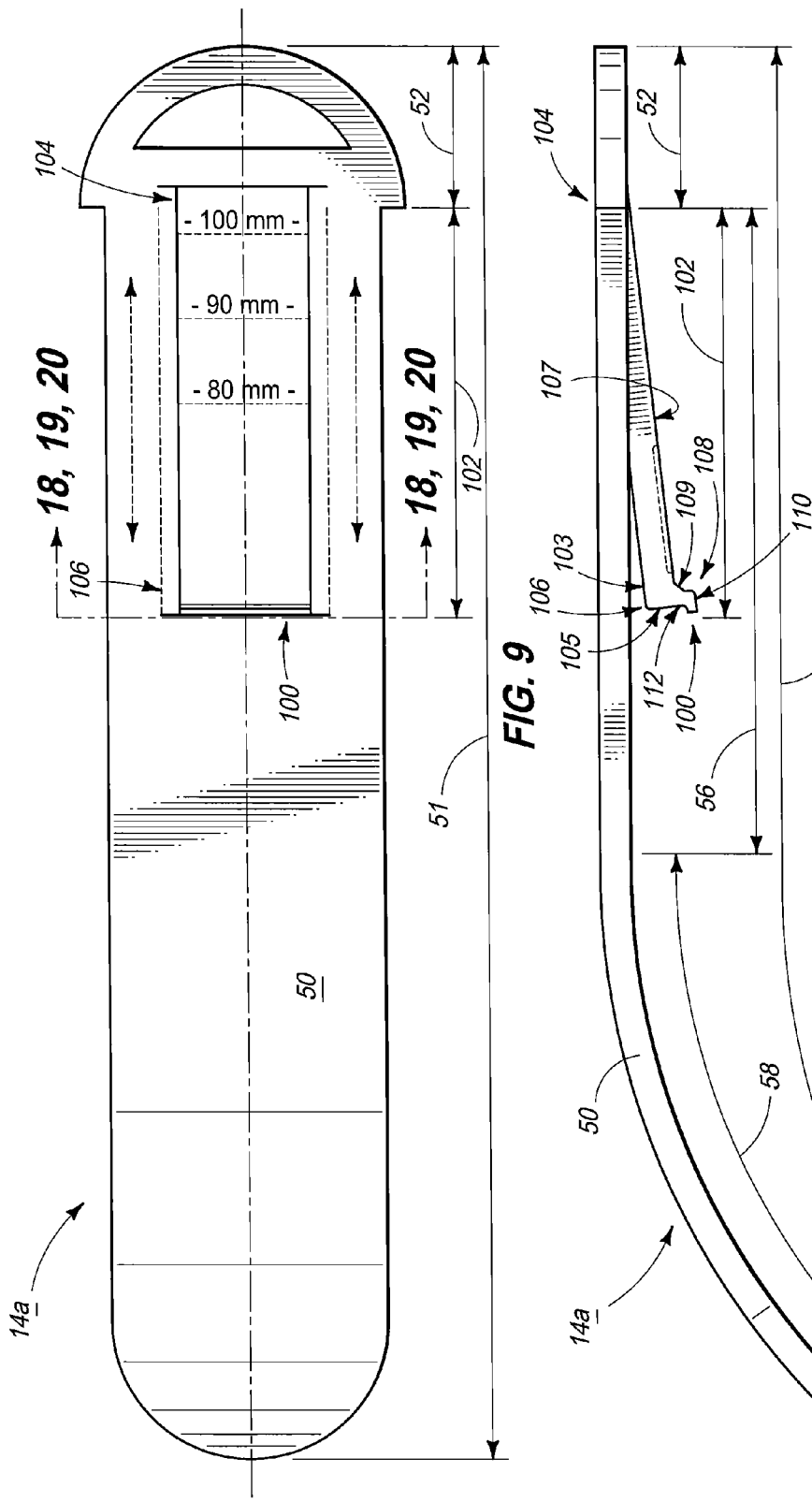

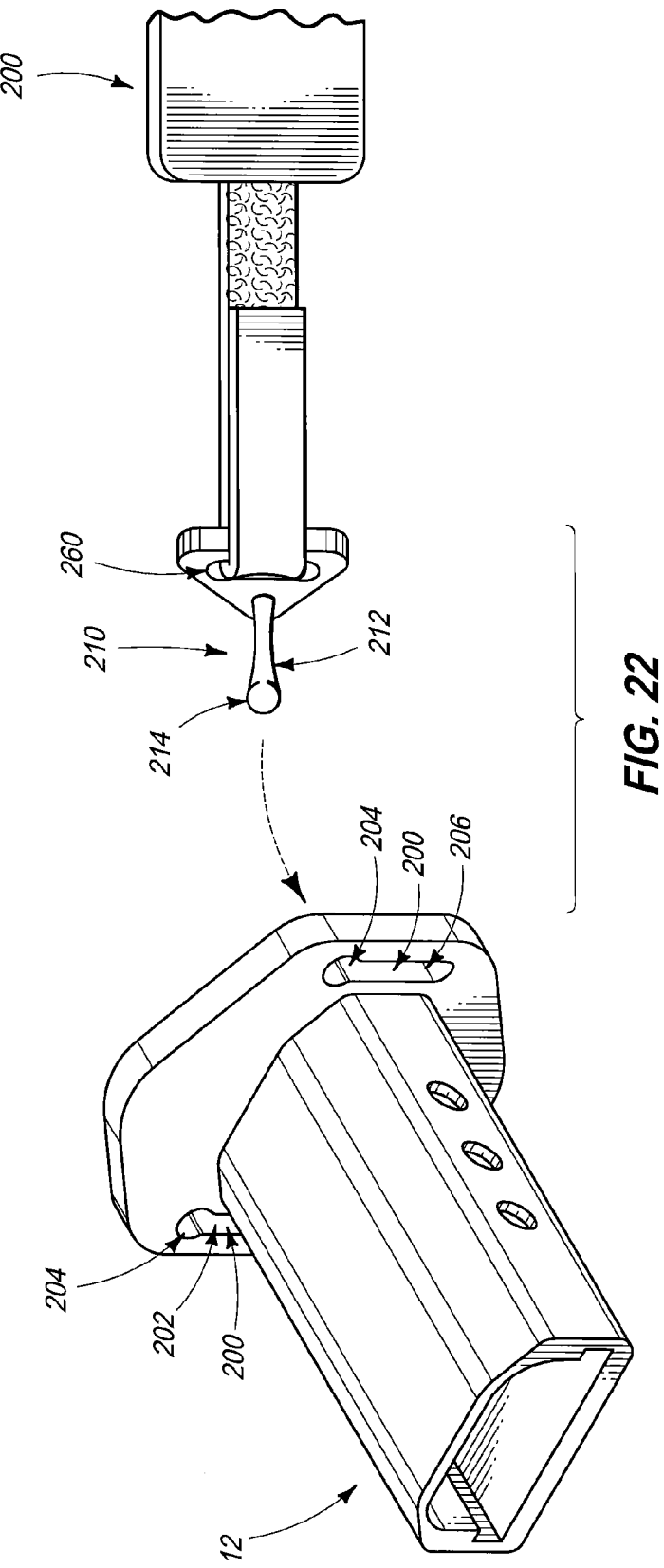

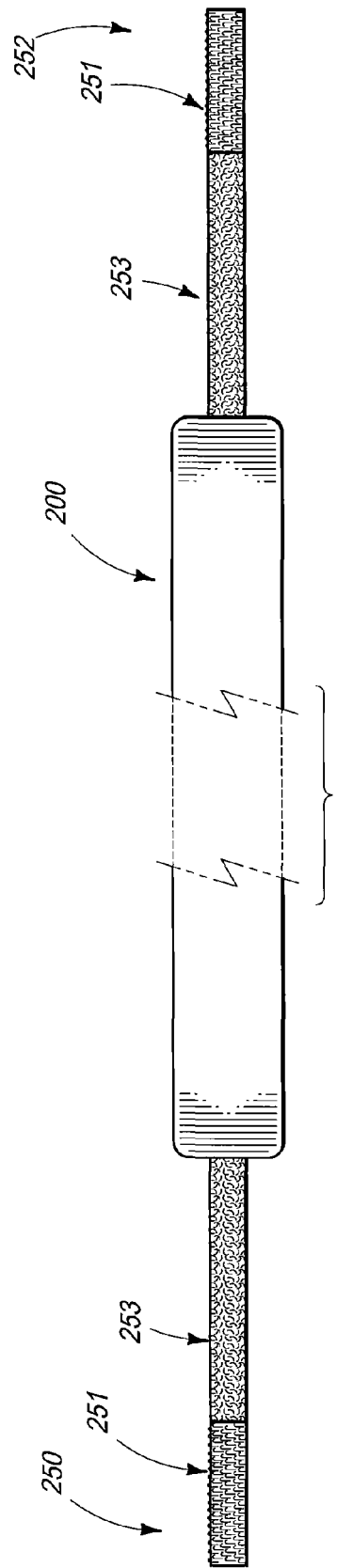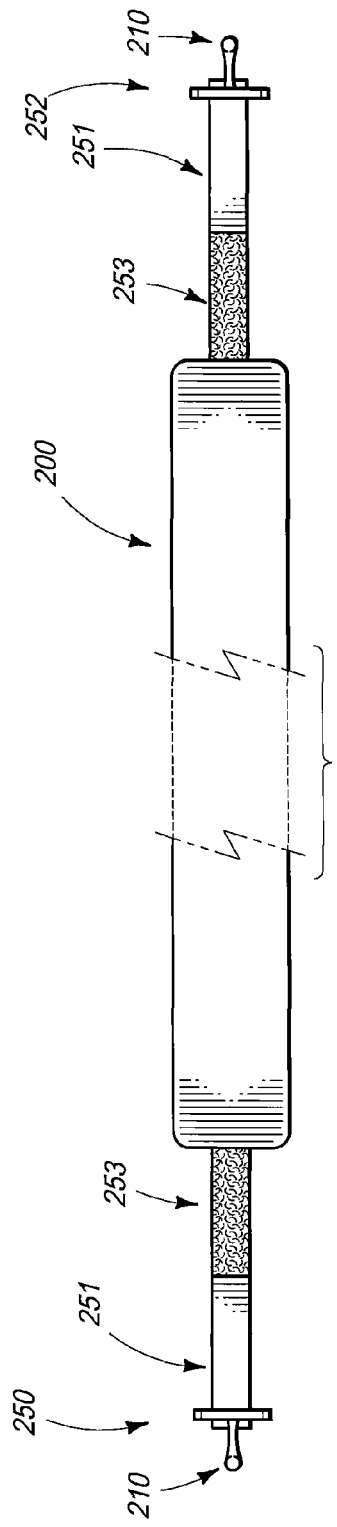

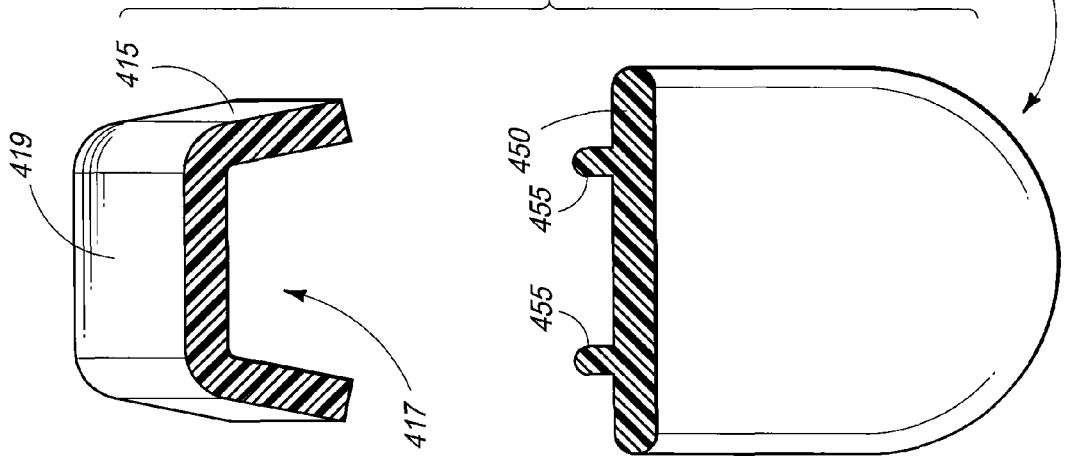
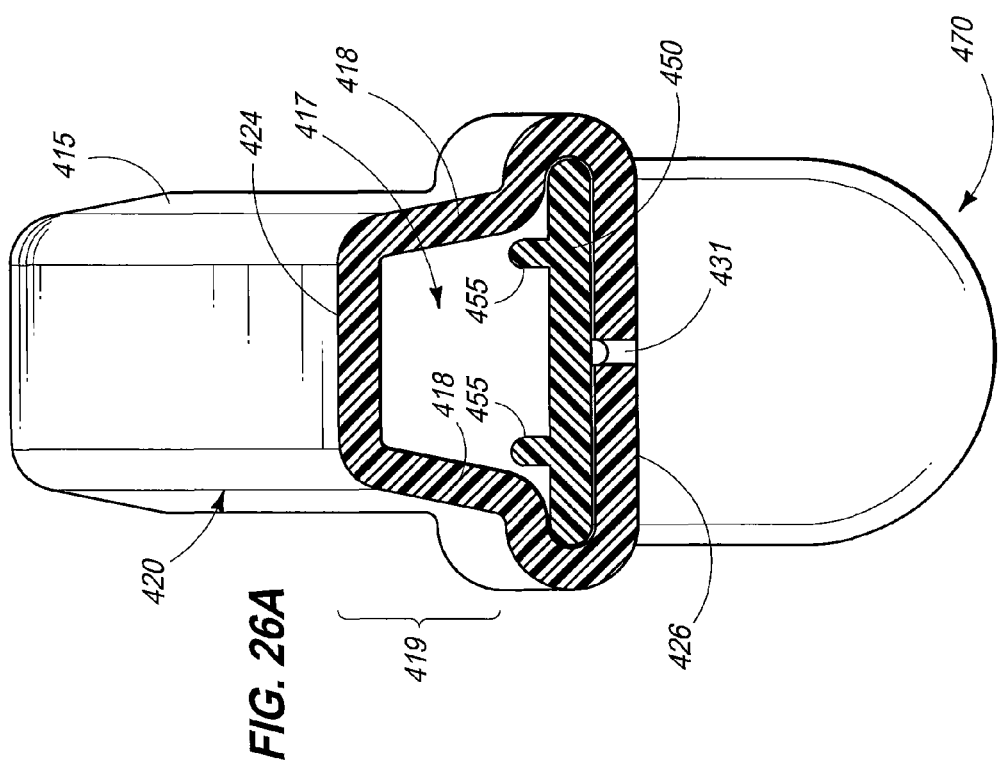

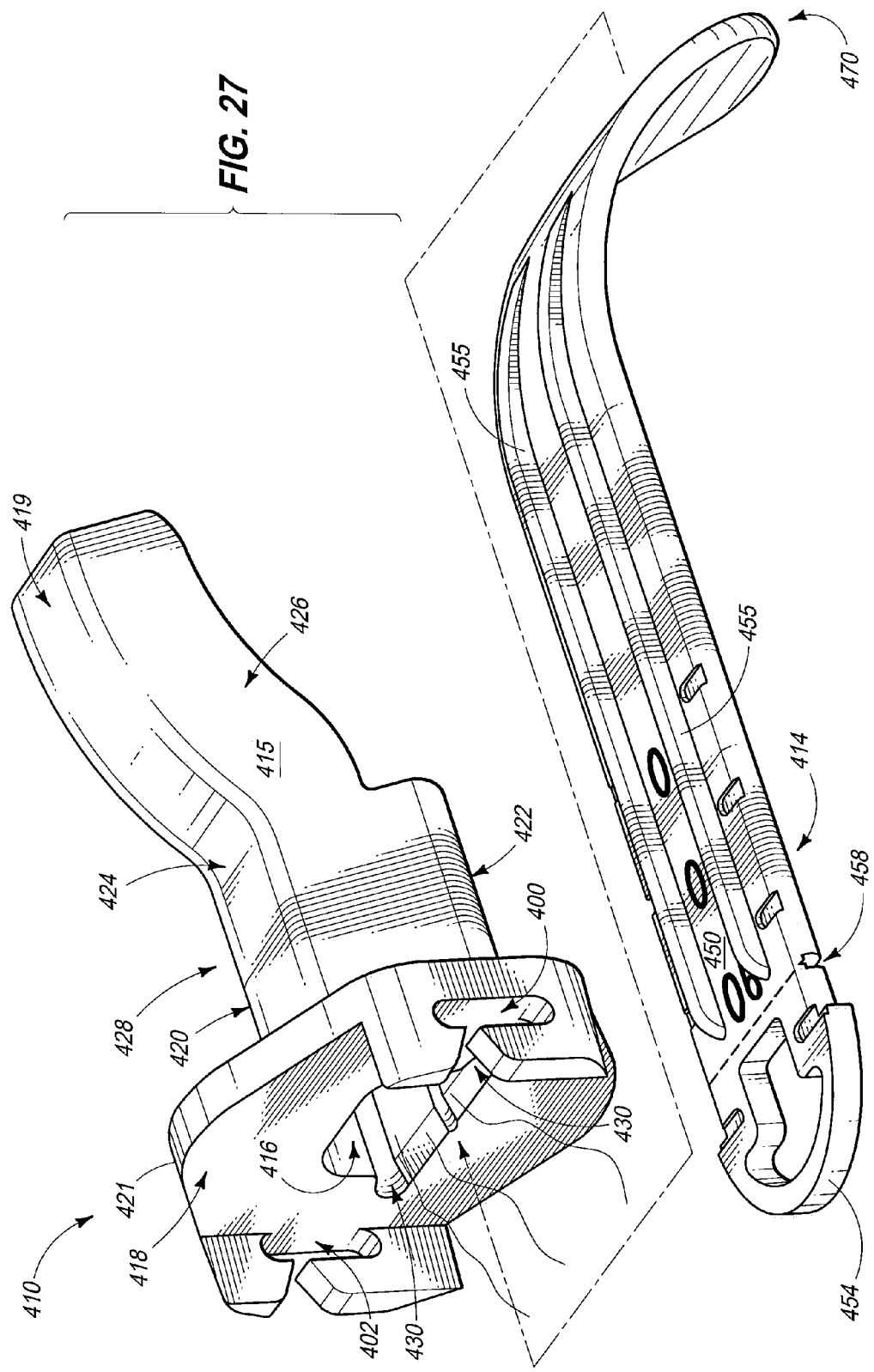

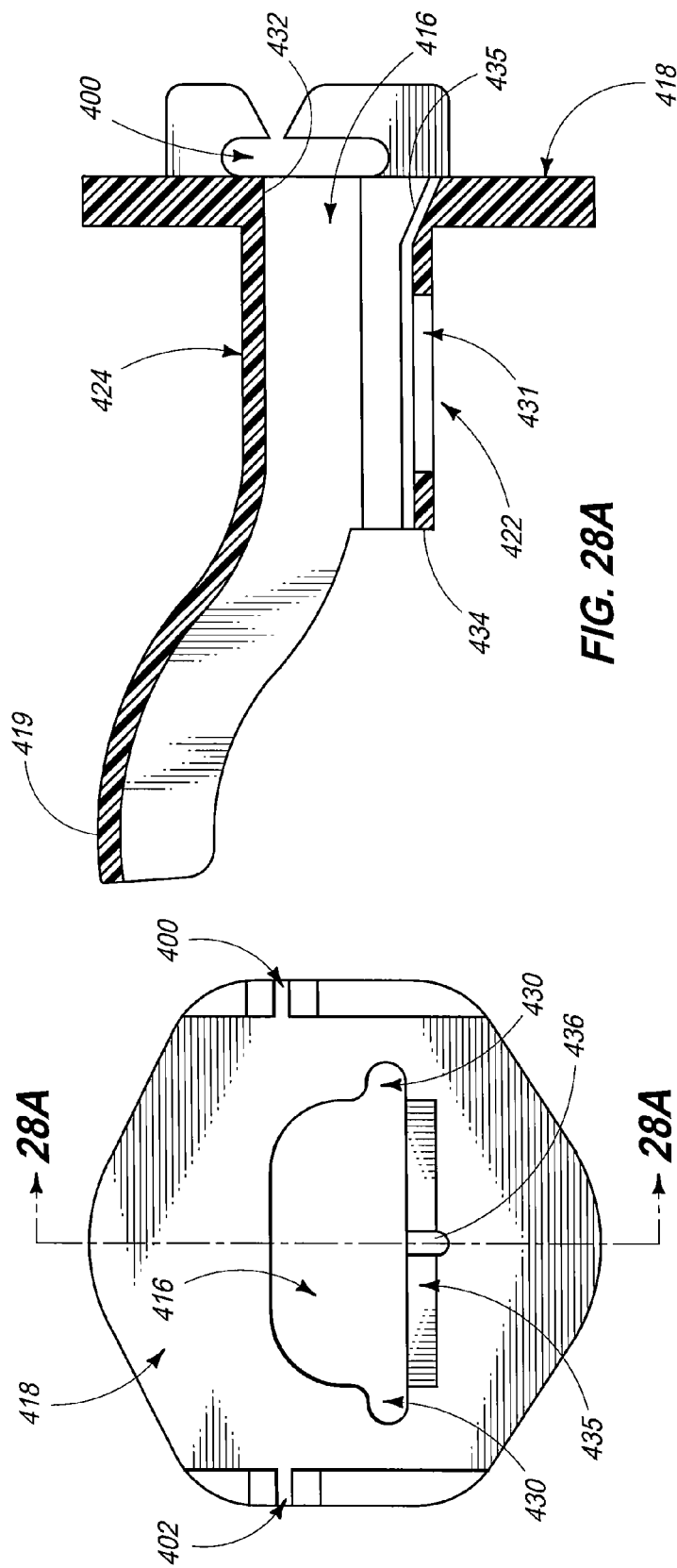

ADJUSTABLE ORAL AIRWAY DEVICES, AND ADJUSTABLE ORAL AIRWAY KITS

RELATED PATENT DATA

This patent application is a Continuation-In-Part Application of U.S. patent application Ser. No. 12/409,022 filed Mar. 23, 2009 entitled "Adjustable Oral Airway Devices, And Adjustable Oral Airway Kits", the entirety of which is hereby incorporated by reference.

TECHNICAL FIELD

Adjustable oral airway devices, and adjustable oral airway kits.

BACKGROUND

Breathing difficulties may occur from severe trauma (such as trauma that may result from a vehicular crash), medical conditions, drug reactions, smoke inhalation, etc. Professional medical emergency response personnel (for instance, paramedics, medevac crews, firefighters, etc.) are thus trained to provide breathing assistance to injured persons. The breathing assistance may include ventilation and oxygenation (with oxygenation comprising administration of oxygen-enriched gas mixtures).

The administration of the ventilation and oxygenation may involve placement of a mask over the injured person's mouth, and/or insertion of a cannula into the injured person's mouth. An oral airway device is often placed in an injured person's mouth prior to utilization of the mask and/or cannula to prevent the soft tissues of the oropharynx (i.e., the part of the throat at the back of the mouth) from collapsing into and obstructing the airway. This can be particularly important if the injured person is unconscious, or in danger of becoming unconscious.

Commercially available oral airway devices often comprise a region that rests between the top and bottom teeth, together with a region having a distal curve (i.e., the blade) to provide support along the back of the palate. The region resting between the teeth may be configured to prevent clenching of the teeth on the tongue, as well as to prevent clenching of the teeth on medical structures (such as, for example, an endotracheal tube, a suction catheter, a fiberoptic laryngoscope, etc.) which may be passed into the oropharynx while the oral airway device is in place.

A problem for medical emergency response personal (e.g., so-called "first responders") is to find an appropriately sized oral airway device for the injured person (or to find appropriately-sized devices for more than one injured person if multiple injured persons are present at a site). If the wrong sized oral airway device is inserted into a person, it may fail to restrain soft tissues (if it is too small for a person's mouth and oropharynx), or may gag and/or choke the person (if it is too large for the person's mouth and oropharynx). Presently, medical emergency response personnel may carry a wide selection of oral airway device sizes and shapes in order to be adequately prepared for numerous different sizes of injured persons. However, stocking of a selection of different sizes of oral airway devices consumes valuable space in a tool kit. It is desired to develop improved oral airway devices that could be used for persons of different sizes, so that a single device could substitute for numerous different sizes of devices.

There has been some effort to develop adjustable oral airway devices. In theory, adjustable oral airway devices could eliminate the need for medical emergency response personnel to stock numerous different sizes of oral airway devices. However, the adjustable oral airway devices utilized by medical emergency response personnel should be suitable for rapid deployment under the stress of emergency situations, and under the awkwardness of the difficult environment conditions that may be encountered by the personnel in emergency situations. In practice, the presently available adjustable oral airway devices tend to be unsuitable for utilization by medical emergency response personnel under the adverse, and time-sensitive, conditions that may be encountered by such personnel. Accordingly, it is desired to develop improved adjustable oral airway devices.

SUMMARY

In one example embodiment, the invention includes an adjustable oral airway device. The device includes a bite block. The bite block has an opening extending therethrough, and has a longitudinal dimension along the opening. The device also includes a tongue deflector extending within the opening through the bite block. The tongue deflector is slideably engaged within the bite block; and is a strip of material comprising a straight region and a curved region. The straight region is at least as long as the longitudinal dimension of the bite block. Additionally, the device includes at least one locking mechanism configured for releasably retaining the tongue deflector in one of two or more predetermined positions within the bite block.

In another example embodiment, the invention includes another adjustable oral airway device. The device includes a bite block portion, a tongue deflector portion slideably engaged within the bite block portion, and at least one locking mechanism configured for releasably retaining the tongue deflector portion in one of two or more predetermined positions within the bite block portion. The device also includes a cannula-receiving region extending through the bite-block portion and along the tongue deflector portion.

In yet another example embodiment, the invention includes an adjustable oral airway kit. The kit includes a bite block. The bite block has an opening extending therethrough, and has a longitudinal dimension along the opening. The kit also includes a tongue deflector configured to extend within the opening through the bite block. The tongue deflector is configured to be slideably engaged within the bite block. The tongue deflector is a strip of material comprising a straight region and a curved region. The straight region is at least as long as the longitudinal dimension of the bite block. Additionally, the tongue deflector and bite block together comprise at least one locking mechanism configured for releasably retaining the tongue deflector in one of two or more predetermined positions within the bite block.

According to another embodiment of the disclosure, oral airway assemblies are provided that can include a body having an opening extending from a first end of the body to a second end of the body. The body can have upper and lower portions in one cross section. The assemblies can include a flange extending from the first end of the body and outwardly from the opening. The assemblies can also include an upper member extending from the upper portion of the second end of the body and outwardly from the opening away from the lower portion. A lower member slidably engaged with the body can also be provided as part of the assemblies. At least a portion of the lower member can extend outwardly from the lower portion of the second end of the body and away from the upper portion when engaged with the body.

Oral airway assemblies are also provided that can include a body having an opening extending from the first end of the body to the second end of the body. The assemblies can include a flange extending from the first end of the body outwardly from the opening. The assemblies can also include a member slidably engaged with the body, with at least a portion of the member extending outwardly from the second end of the body, and the member further comprising a tab at one end, the tab being pivotably coupled to the member.

BRIEF DESCRIPTION OF THE DRAWINGS

FIGS. 4 and 5 are a top view, and a side view, respectively, of the tongue deflector portion of the adjustable oral airway device of FIG. 1.

FIGS. 9 and 10 are a top view, and a side view, respectively, of another embodiment of a tongue deflector portion of an adjustable oral airway device.

FIG. 22 shows a portion of a headband oriented for engagement with a slot in an example bite block portion of an adjustable oral airway device.

FIG. 23 shows a headband having hook and loop (e.g. VELCRO™) attachment regions at a pair of opposing ends.

FIG. 24 shows the headband of FIG. 23 after utilization of the hook and loop attachment regions to retain a pair of projecting stems to the headband.

FIG. 26A is a cross section view of the airway assembly of FIG. 26.

FIG. 26B is another cross section view of the airway assembly of FIG. 26.

FIG. 27 is an exploded view of the airway assembly of FIG. 26.

FIG. 28 is a view of an elevation of a component of the airway assembly of FIG. 26.

FIG. 28A is a cross section view of the component of the assembly of FIG. 26.

DETAILED DESCRIPTION OF THE ILLUSTRATED EMBODIMENTS

As discussed above in the "Background" section of this disclosure, a prior art problem exists with respect to conventional devices utilized for maintaining the oral airways of patients in an emergency applications. Specifically, the conventional devices are either non-adjustable so that numerous different sizes of devices must be carried by medical emergency response personnel to accommodate the different sizes of individuals that may be in need of aid; or, to the extent adjustable devices exist in the prior art, such tend to be awkward to utilize with the speed and efficiency desired in emergency applications.

In some embodiments, the invention includes adjustable oral airway devices that are convenient to utilize by medical emergency response personnel under the difficult conditions that they may encounter.

Figure 1:
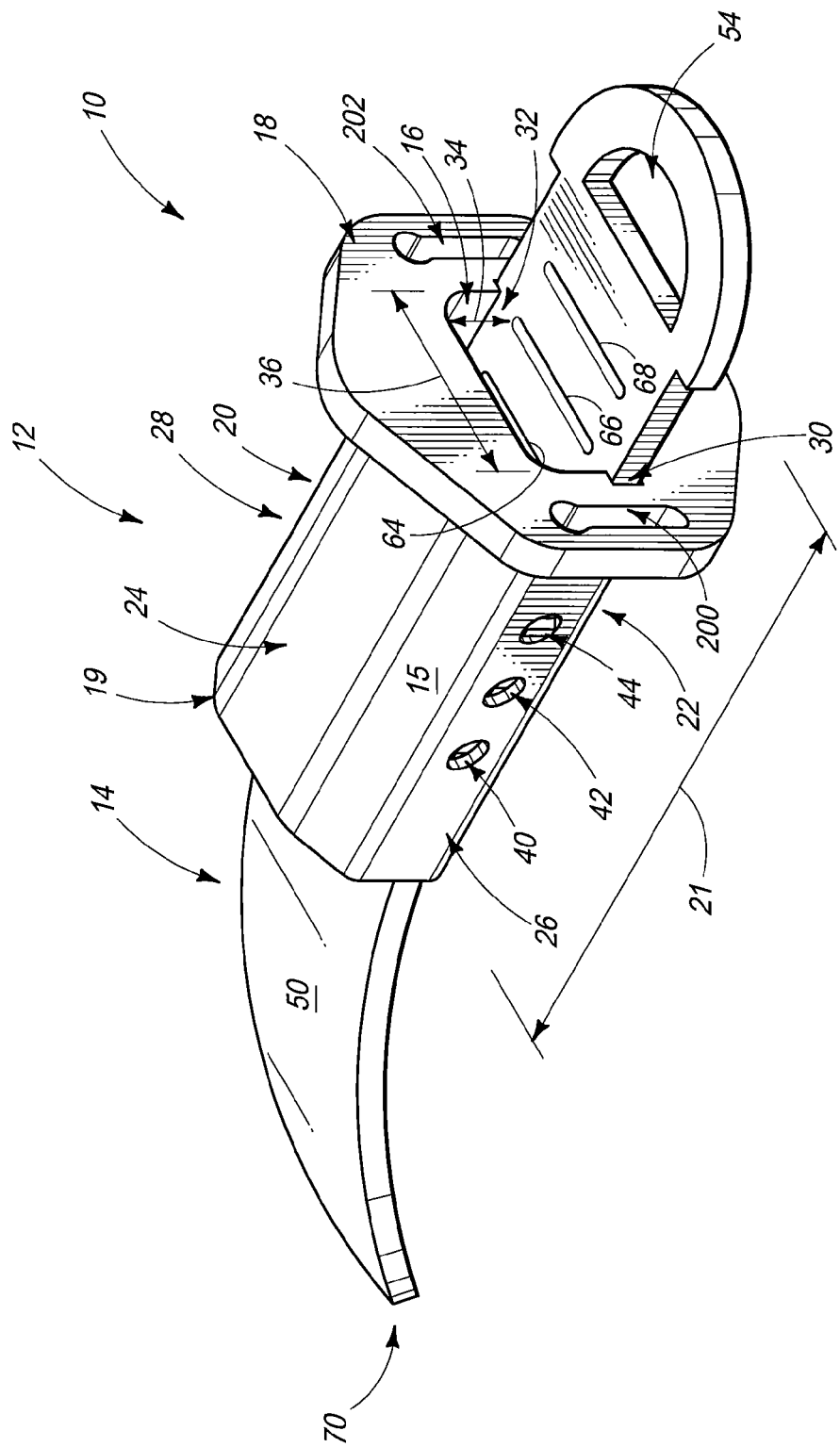
FIG. 1 is a three-dimensional view of an example adjustable oral airway device.
Figure 2:
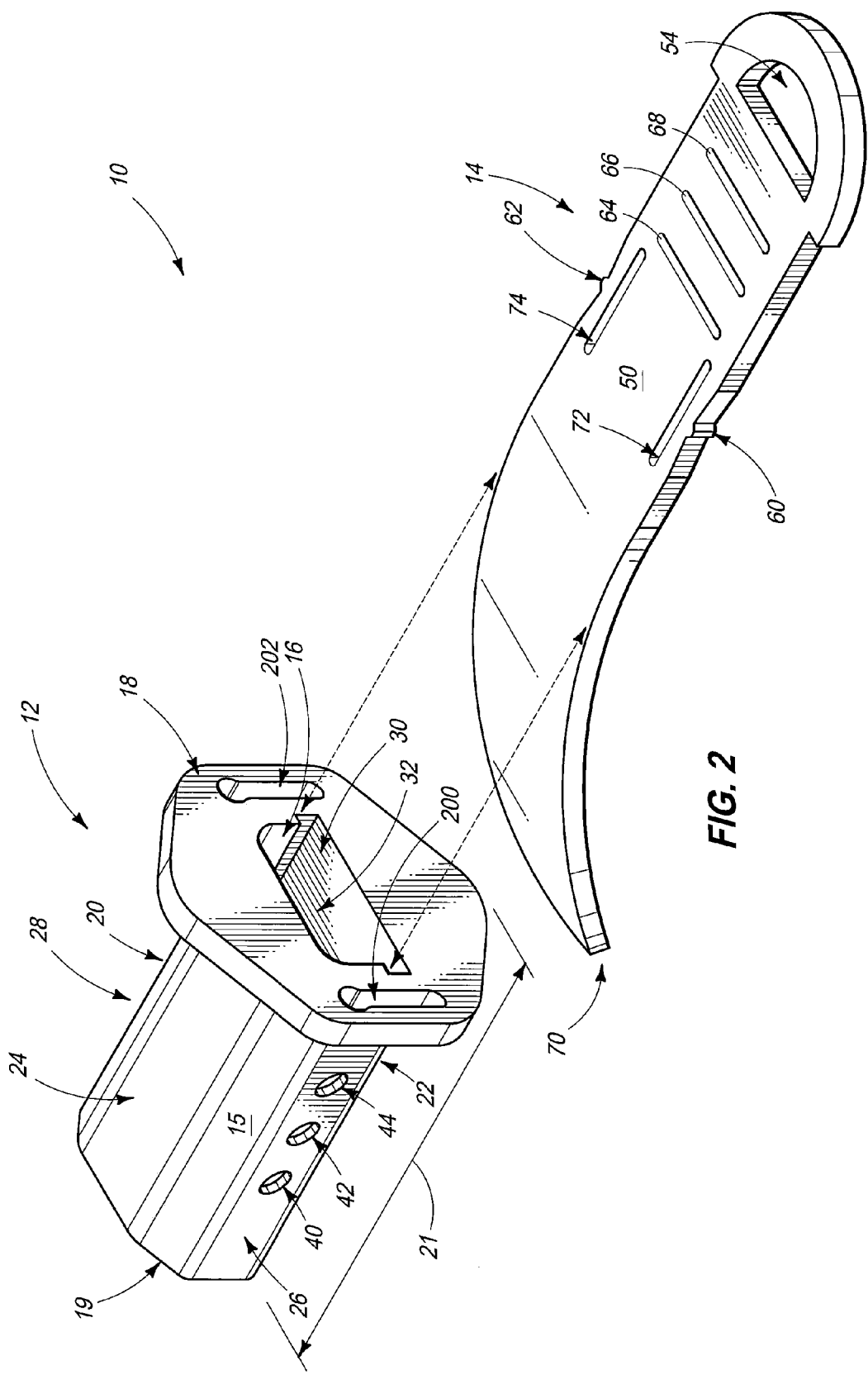
FIG. 2 is an exploded view of the example adjustable oral airway device of FIG. 1.

An example adjustable oral airway device 10 is shown in FIGS. 1 and 2. The adjustable oral airway device may be referred to as a Dual Air System™. The device 10 comprises two primary components—a bite block 12 and a tongue deflector 14. FIG. 1 shows the tongue deflector 14 slideably engaged within an opening 16 in the bite block 12; and FIG. 2 shows the tongue deflector 14 separate from the bite block 12. The tongue deflector and bite block may be completely separate components relative to one another (as shown); or in other embodiments (not shown) may be connected to one another through a tether or other suitable means. In some embodiments, the bite block 12 and tongue deflector 14 may be considered to be portions of the oral airway device 10; and accordingly may be referred to as a bite block portion and a tongue deflector portion, respectively.

Figure 3:
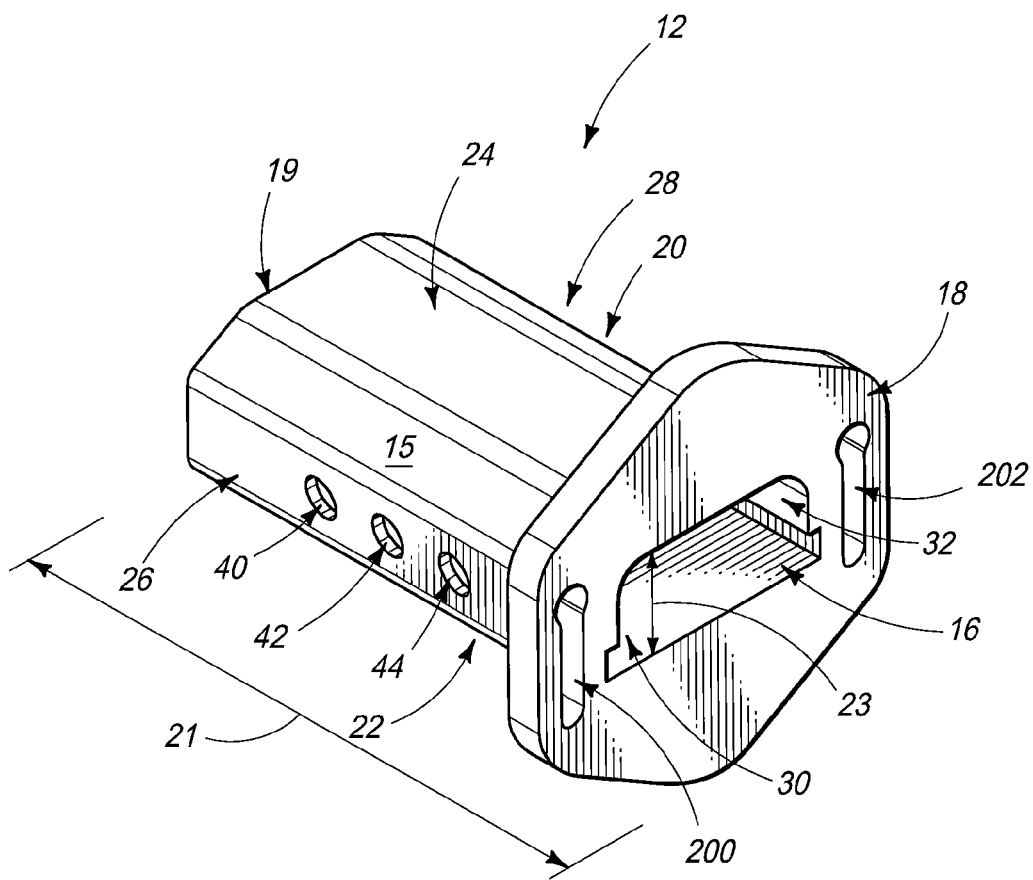
FIG. 3 is a view of the bite block portion of the adjustable oral airway device of FIG. 1.

The bite block 12 is shown in combination with the tongue deflector 14 in FIGS. 1 and 2, and is shown in isolation in FIG. 3. The bite block includes a planar surface 18 around the opening 16, and includes a bitable region 20 adjacent the planar surface 18. In operation, the bitable region is placed between the teeth of a person, and the planar surface 18 is outward of the lips of the person. The bite block comprises a material 15. In some embodiments, such material may comprise, consist essentially of, or consist of polypropylene, such as polypropylene approved for use in medical devices by the Environmental Protection Agency (EPA) and/or the Food and Drug Administration (FDA).

The opening 16 extends longitudinally through the planar surface 18 and through the bitable region 20 of the bite block 12.

The bite block may be considered to comprise a floor 22 beneath opening 16, a top 24 over the opening 16, and a pair of opposing sides 26 and 28 extending from the floor to the top along the sides of the opening 16.

The planar surface 18 may be considered to be a front surface of the bite block, and the bite block may be considered to comprise a back surface 19 in opposing relation to such front surface. The bite block has a longitudinal dimension 21 extending from the front surface 18 to the back surface 19; or, in other words, has a longitudinal dimension extending along opening 16. Such longitudinal dimension may be, for example, from about 4 centimeters to about 5 centimeters, in some embodiments. The bitable region 20 may have a length of from about 3.8 centimeters to about 4.8 centimeters in such embodiments.

The opening 16 has a height 23 between the floor 22 of the bite block and the top 24 of the bite block. A lower region of the opening 16 is a slot 30 configured for receipt of the tongue deflector 14, and an upper portion of the opening may be configured as a cannula-receiving region 32 (as explained in more detail below with reference to FIG. 7).

FIG. 1 shows the tongue deflector 14 received within the slot region 30 of opening 16, and shows that the cannula-receiving region 32 of the opening is over the tongue deflector. The cannula-receiving region may have any suitable shape, but it may be advantageous for there to be enough room in the cannula-receiving region to receive one or more cannulas, and to provide ample airspace adjacent the cannulas for ventilation to occur through the bite block while the one or more cannulas are in place. The cannula-receiving region may be substantially rectangular (as shown).

FIG. 1 shows that the cannula-receiving region 32 has a height 34 and a width 36. In some embodiments, the cannula-receiving region 32 may be at least three times as wide as it is tall. For instance, in some embodiments the height of the cannula-receiving region may be about 0.6 centimeters, and the width may be about two centimeters.

Bite block 12 comprises a pair of receptacles 200 and 202 extending through planar surface 18. Such receptacles may be utilized for connecting the bite block to a headband as discussed below with reference to FIGS. 22 and 25.

Figure 8:
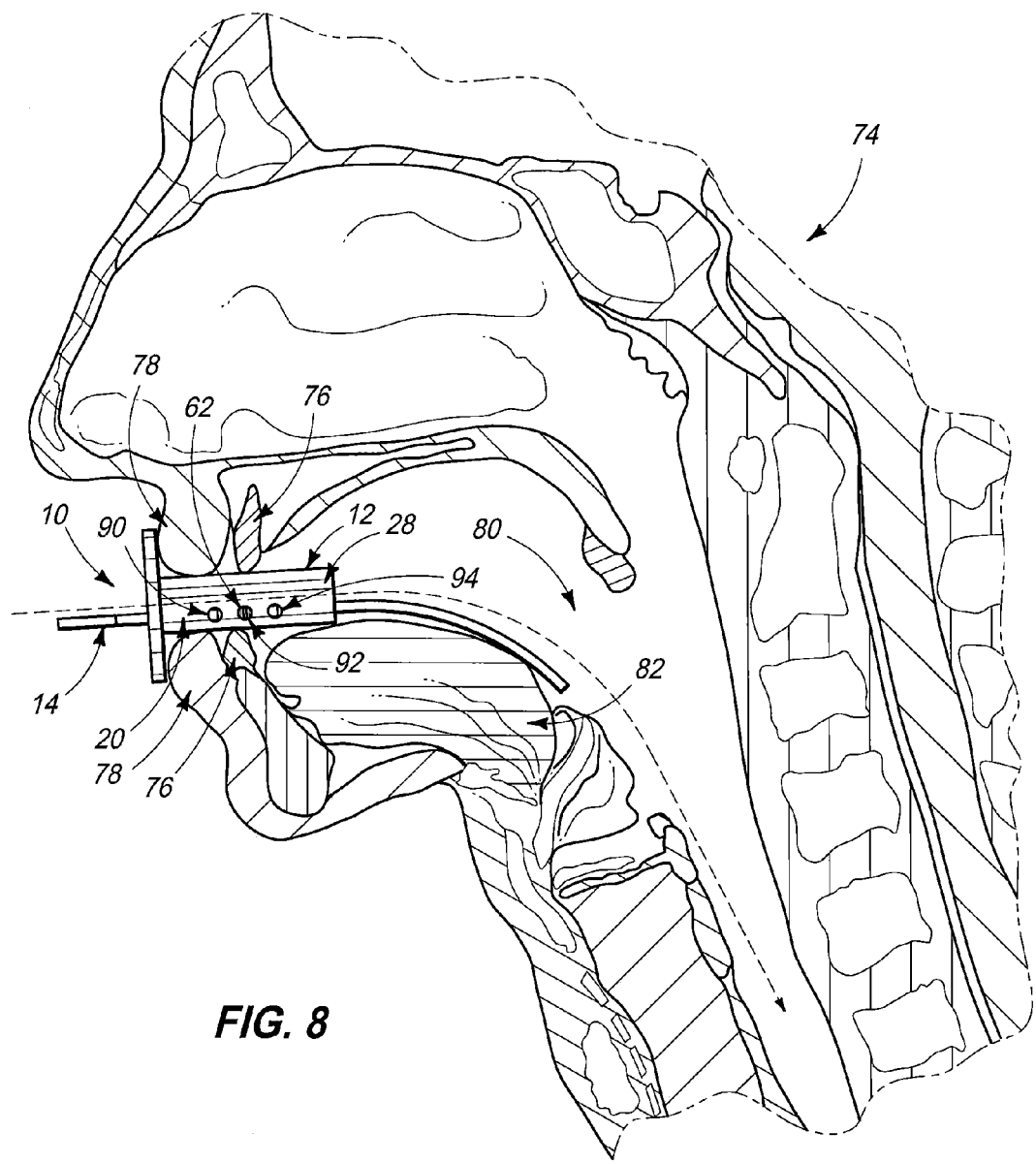
FIG. 8 is a cross sectional view of a person's lower head and upper throat, showing the example adjustable oral airway device of FIG. 1 utilized to provide an oral airway for the person.

The bite block 12 has a plurality of cavities 40, 42 and 44 extending through the side 26 of the bite block. In some embodiments, the side 28 of the bite block will be a mirror image of the side 26 (as shown in FIG. 8), and accordingly will also have multiple cavities extending therethrough. In the shown embodiment, there are three cavities extending through the side 26. Each of the cavities represents a predetermined position where the tongue deflector may be locked into the bite block. The number of cavities may thus be chosen based upon the number of predetermined locking positions that are desired. There may be some applications in which is desired to have a large number of predetermined locking positions so that the location of the tongue deflector may be finely controlled. In other applications, it may be desired to have fewer predetermined locking positions so that the location of the tongue deflector is more coarsely controlled. It may be faster to adjust the tongue deflector to a desired location if there are fewer predetermined locking positions, but there will be a trade-off relative to the degree to which the adjustable oral airway device 10 may be tailored to specific mouth/throat sizes. There will generally be at least two predetermined locking positions associated with adjustable oral airway devices of the present invention.

Although the cavities 40, 42 and 44 are shown to extend entirely through the side 26 of bite block 12, in other applications the cavities may be dents formed along the interior of the wall (in other words, along opening 16) rather than being formed to extend entirely through the wall.

The tongue deflector 14 is shown in combination with the bite block 12 in FIGS. 1 and 2, and is shown in isolation in FIGS. 4 and 5. The tongue deflector comprises a material 50. Such material may be a pliable material, and in some embodiments may comprise, consist essentially of, or consist of polypropylene, such as polypropylene approved for use in medical devices by the Environmental Protection Agency (EPA) and/or the Food and Drug Administration (FDA).

The tongue deflector has a length 51, a width 53, and a thickness 55, as shown in FIGS. 4 and 5. In some embodiments, the length may be from about 11 centimeters to about 13 centimeters; the width may be from about 1.5 centimeters to about four centimeters; and the thickness may be less than or equal to about 0.2 centimeters.

A segment 52 of the length corresponds to a loop 54 configured to enable grasping by the fingers of a person operating the adjustable oral airway device 10. In some embodiments, segment 52 may have a length of from about one centimeter to about two centimeters. The loop 54 may be omitted in some embodiments.

FIG. 5 shows that the length 51 of the tongue deflector 14 may be considered to be sub-divided into three segments. One of the segments is the segment 52 discussed above as corresponding to loop 54. Another of the segments is a straight region 56, while the remaining segment corresponds to a curved region 58. The straight region 56 is utilized for adjustment of the tongue deflector location within the bite block 12, and the curved region 58 is utilized for retaining the tongue and/or other soft mouth/throat tissue of a patient. The straight region may be at least as long as the longitudinal dimension 21 of the bite block 12.

The tongue deflector 14 comprises a pair of deflectable protuberances 60 and 62 along the opposing sides of the tongue deflector. In operation, such protuberances engage within the cavities in the sidewalls of bite block 12 (for instance, cavities 40, 42 and 44 in the sidewall 26 of the bite block, and similar cavities in the opposing sidewall 28 of the bite block) to releasably retain the tongue deflector in the predetermined positions defined by the cavities. For instance, protuberance 60 may be seated within any one of the cavities 40, 42 and 44 to releasably retain the tongue deflector in a predetermined position.

The illustrated tongue deflector has marks 64, 66 and 68 which may be aligned to the planar surface 18 of the bite block 12 to identify to a user when the tongue deflector is engaged in a specific predetermined position. The tongue deflector has an end 70 which will be at the deepest location in a patient's throat during utilization of the adjustable oral airway device 10. The adjustable oral airway device may be provided with instructions, or with additional markings on one or both of the bite block and tongue deflector, which identify to the operator of the device the overall depth to which end 70 extends when the tongue deflector is in the predetermined positions identified by markings 64, 66 and 68.

Although three alignment markings 64, 66 and 68 are shown, in other embodiments there may be less than three alignment markings, and in yet other embodiments there may be more than three alignment markings. Generally, there will be at least two alignment markings corresponding to the at least two predetermined positions that the tongue deflector may be locked in relative to the bite block.

In the shown embodiment, tongue deflector 14 has a pair of slots 72 and 74 extending through the tongue deflector adjacent protuberances 60 and 62, respectively. The slots enable protuberances 60 and 62 to flex inwardly during adjustment of the tongue deflector within the bite block. The material 50 of the tongue deflector provides sufficient outward bias to the protuberances 60 and 62 so that the protuberances will lock within the cavities in the bite block when the protuberances are aligned with such cavities.

Although the illustrated tongue deflector has two protuberances, in other embodiments there may be only one protuberance utilized, and in yet other embodiments there may be more than two protuberances utilized.

The protuberances on the tongue deflector (i.e., the protuberances 60 and 62), together with the cavities in the bite block (for instance, cavities 40, 42 and 44) define a locking mechanism configured for releasably retaining the tongue deflector in one of two or more predetermined positions within the bite block.

Figure 6:
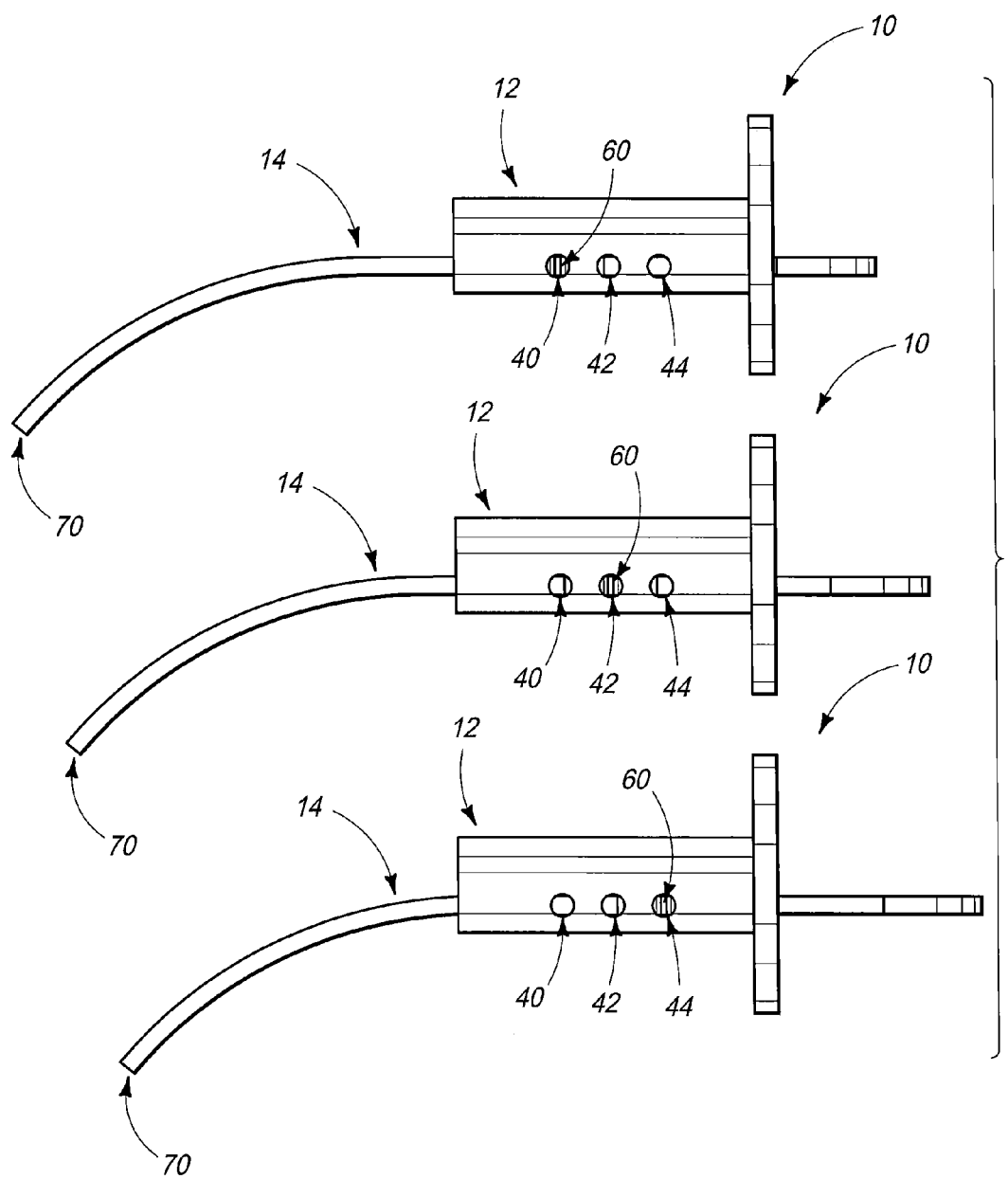
FIG. 6 shows side views of the example adjustable oral airway device of FIG. 1 at three different size adjustments.

FIG. 6 shows adjustable oral airway device 10 at three different size adjustments corresponding to the three different predetermined locations defined by cavities 40, 42 and 44. Specifically, a topmost orientation of the adjustable oral airway device shows the protuberance 60 of the tongue deflector 14 engaged within cavity 40, and thus shows the end 70 of the tongue deflector at the deepest predetermined location of the device 10. The next orientation down shows the protuberance 60 pulled into cavity 42, and thus shows the end 70 of the tongue deflector at a predetermined location that is less deep than that of the topmost orientation of device 10 in FIG. 6. The bottom orientation of the adjustable oral airway device shows the protuberance 60 engaged within cavity 44, and thus shows the end 70 of the tongue deflector at the shallowest predetermined location of the device 10.

Figure 7:
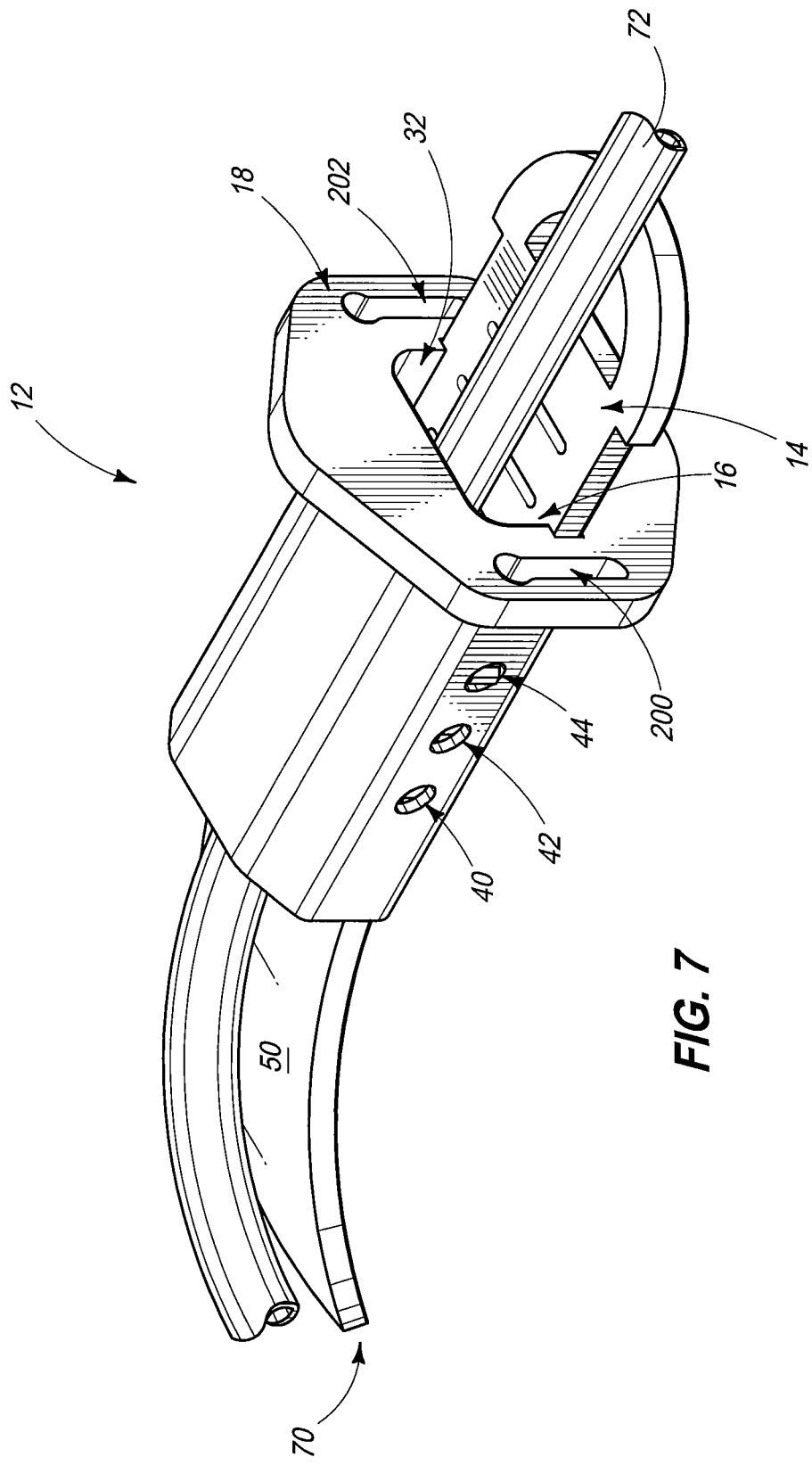
FIG. 7 is a view of the adjustable oral airway device of FIG. 1 together with a cannula extended within an opening within the adjustable oral airway device.

FIG. 7 shows a cannula 72 extending through bite block 12 within the cannula-receiving region 32 of opening 16. FIG. 7 also shows that in some embodiments there may be a significant amount of space available within the cannula-receiving region 32 after a cannula is inserted within such region. Such may enable multiple devices and/or cannulas to extend simultaneously through the bite block, and/or may enable ventilation to be provided through the bite block after one or more cannulas and devices are inserted through the cannula-receiving region.

FIG. 8 shows adjustable oral airway device 10 in operation, and specifically shows the device within the mouth and throat of a patient 74. The bitable region 20 of the bite block is between the teeth 76 of the upper and lower jaws of the patient, and also between the lips 78 of the patient. The device 10 has a large surface exterior of the patient's mouth, which can prevent the device from falling into the patient's mouth. The tongue deflector 14 extends into the upper throat 80 of the patient and holds down soft tissues 82 within the upper throat.

In practice, a mask (not shown) will typically be provided over the patient's mouth, and thus over the adjustable oral airway device 10. The mask may be used in bag valve mask ventilation. The opening 16 through the adjustable oral airway device 10 can provide, among other things, a route for ventilation between the mask and the patient's lungs, a path for a breathing tube to be inserted into a patient's mouth, a path for a flexible camera to be inserted into a patient's throat, and/or a path for a suction device to be inserted into a patient's mouth or throat.

One of the advantages of the invention is that if the patient 74 becomes conscious and is uncomfortable with the tongue deflector 14 and/or starts to gag on the tongue deflector, the tongue deflector may be retracted from the throat and pulled entirely out of the bite block, while leaving the bite block in place. Ventilation may continue to be provided through the opening 16 in the bite block after the tongue deflector is removed.

The view of bite block 10 in FIG. 8 is rotated relative to the view of FIGS. 1, 2 and 5, and accordingly side 28 is visible in FIG. 8. Side 28 is shown comprising cavities 90, 92 and 94 analogous to the cavities 40, 42 and 44 (FIG. 1) of side 26; and the protuberance 62 of tongue deflector 14 is shown engaged within the cavity 92.

The adjustable oral airway device 10 of FIGS. 1-8 comprises an embodiment of a locking mechanism in which protuberances along the side of a tongue deflector (specifically, the protuberances 60 and 62 shown in FIG. 4) engage within cavities in the sidewall of the bite block (specifically, the cavities 40, 42, 44, 90, 92 and 94 of FIGS. 1 and 8). In other embodiments, other locking mechanisms may be utilized.

FIGS. 9 and 10 illustrate a tongue deflector 14a of an example embodiment in which the locking mechanism includes a deflectable region 100 that extends downwardly from within a center of the tongue deflector. The tongue deflector 14a comprises the length 51 discussed above with reference to FIGS. 7 and 8, and comprises the segments 52, 56 and 58 of such length. Segment 52 is a handle, segment 56 is a straight region, and segment 58 is a curved region. In the shown embodiment, the deflectable protuberance 100 is within the straight region 56 of the tongue deflector.

The deflectable region 100 is along a length 102 of a deflectable material of the tongue deflector. Such length comprises a first end 104 where the deflectable material joins to the rest of tongue deflector 14a, and an opposing second end 106 which may be deflected downwardly from a central region of the tongue deflector. The second end 106 has a primary end surface 105 that is substantially orthogonal to an upper surface of the deflectable material of the tongue deflector. An engagement structure (which may be considered to be a deflectable protuberance) 108 extends downwardly from surface 105, and extends below a bottom surface 107 of the deflectable material. The engagement structure has an "L" shape, and specifically includes a lower base region 110 joining to a stem region 112. One surface of the stem region corresponds to the surface 105, and an opposing surface of the stem region includes a surface 109 that is angled relative to bottom surface 107. In operation, the engagement structure 108 corresponds to a protuberance that may be releasably retained in cavities formed along a bottom of a bite block.

Figure 12:
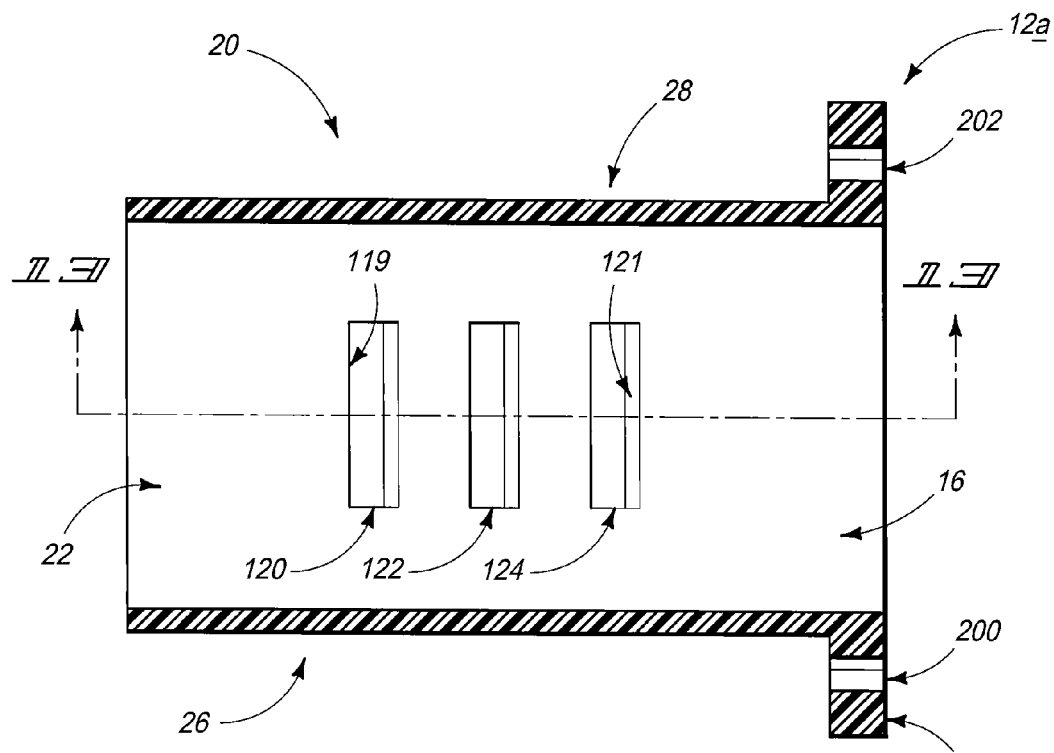
Figure 13:
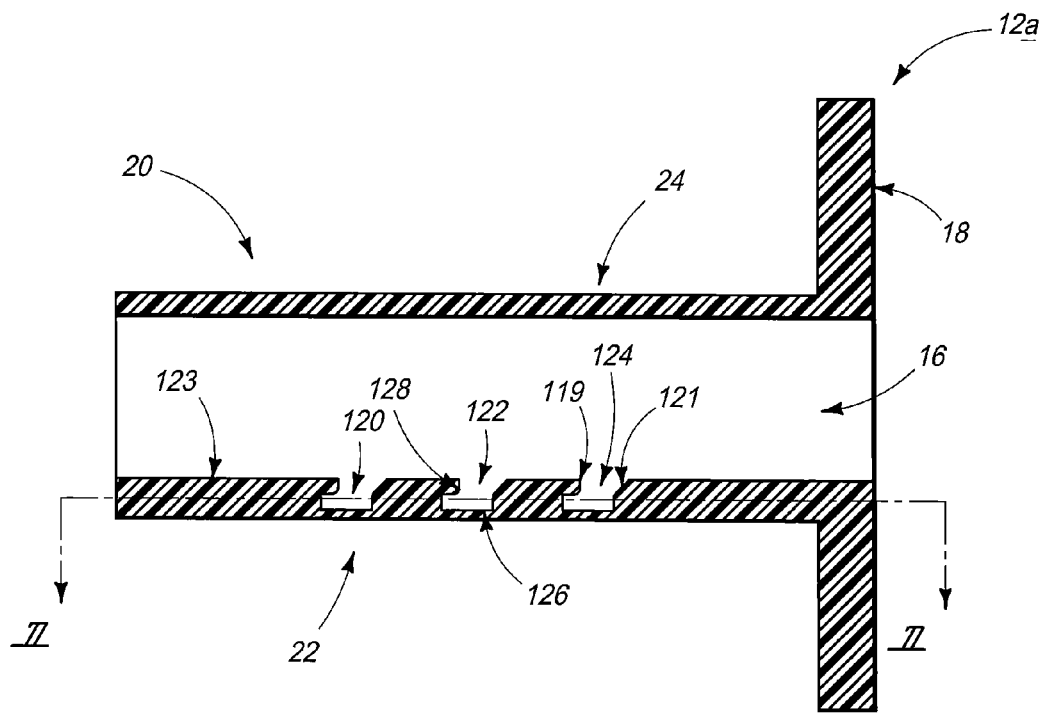

FIGS. 12-13 illustrate an example bite block 12a which may be utilized in conjunction with the tongue deflector 14a of FIGS. 9 and 10.

Figure 11:
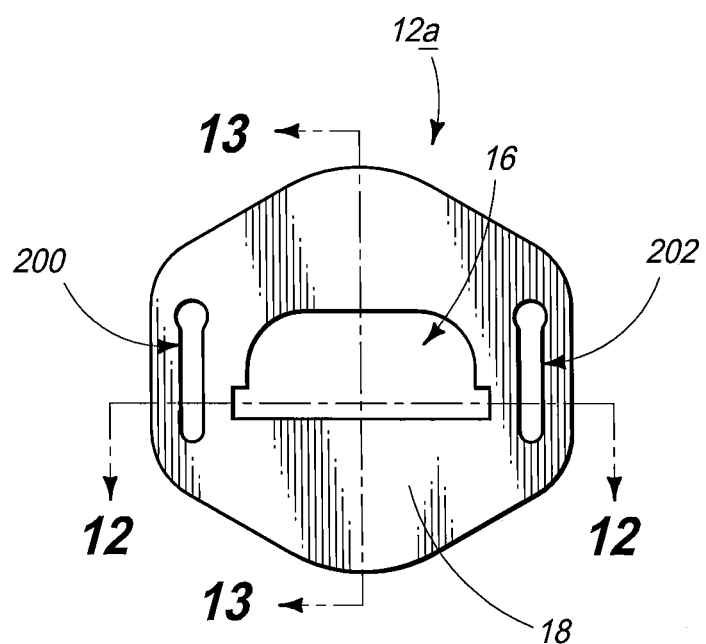
FIGS. 11-13 are a front view, cross sectional top view, and cross sectional side view, respectively, of an embodiment of a bite block portion that may utilized with the tongue deflector portion of FIGS. 9 and 10 to form an adjustable oral airway device. The view of FIG. 12 is along the lines 12-12 of FIGS. 11 and 13, and the view of FIG. 13 is along the lines 13-13 of FIGS. 11 and 12.

Bite block 12a includes the planar surface 18 discussed above in FIG. 1 with reference to bite block 12, and includes the bitable region 20 adjacent such planar surface. The bite block 12a also includes the opening 16, the floor 22 beneath the opening, the top 24 over the opening, and the opposing sides 26 and 28 extending from the floor to the top along the sides of the opening. However, in contrast to the bite block 12 of FIG. 1, the bite block 12a of FIGS. 11-13 does not include cavities 40, 42 and 44 along the sidewalls, but instead includes cavities 120, 122 and 124 extending into the floor 22.

The cavities 120, 122 and 124 are complementary to retaining structure 108, and accordingly comprise "L" shapes. Such "L" shapes include a base region 126 and a stem region 128. The stem region 128 includes a surface 119 that is substantially orthogonal to an upper surface 123 of the floor, and includes a surface 121 that is sloped (i.e., not orthogonal) relative to the upper surface 123 of the floor.

The tongue deflector 14a may comprise the same material 50 discussed above with reference to tongue deflector 14 of FIG. 1, and the bite block 12a may comprise the same material 15 discussed above with reference to the bite block 12 of FIG. 1.

FIGS. 14-17 illustrate utilization of deflectable region 100 relative to cavities 120, 122 and 124. The deflectable region 100 is shown in isolation from the rest of tongue deflector 14a to simplify the drawings, but it is to be understood that the deflectable region would be part of the tongue deflector 14a described in FIGS. 9 and 10.

Figure 14:
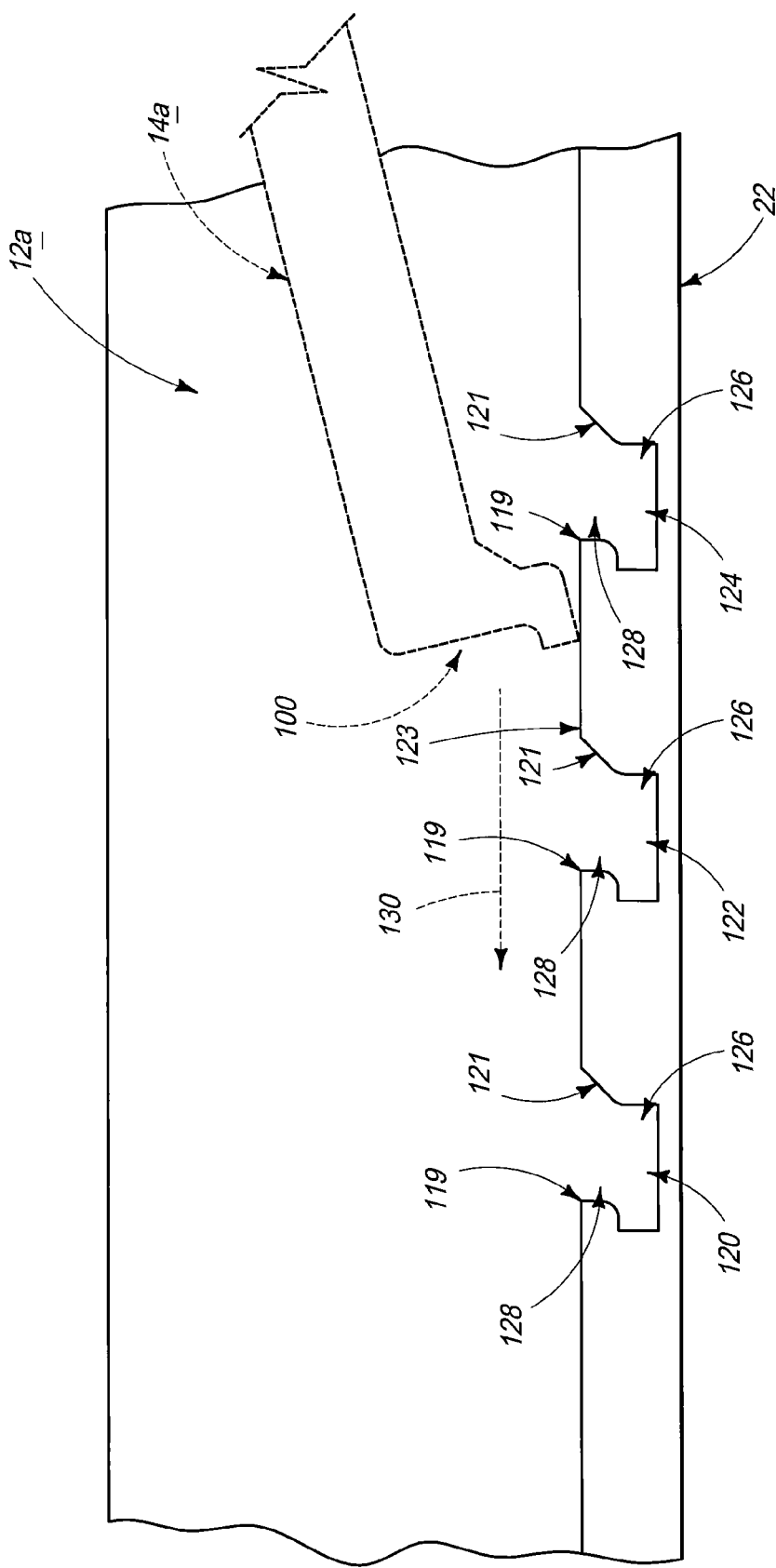
FIGS. 14-17 are cross sectional side views showing the tongue deflector portion of FIGS. 9 and 10 engaged in the bite block portion of FIGS. 11-13 at various stages of adjustment of an adjustable oral airway device.

FIG. 14 shows the deflectable region 100 sliding across a surface 123 along the floor 22 of bite block 12a, with a direction of movement of region 100 being indicated with arrow 130.

Figure 15:
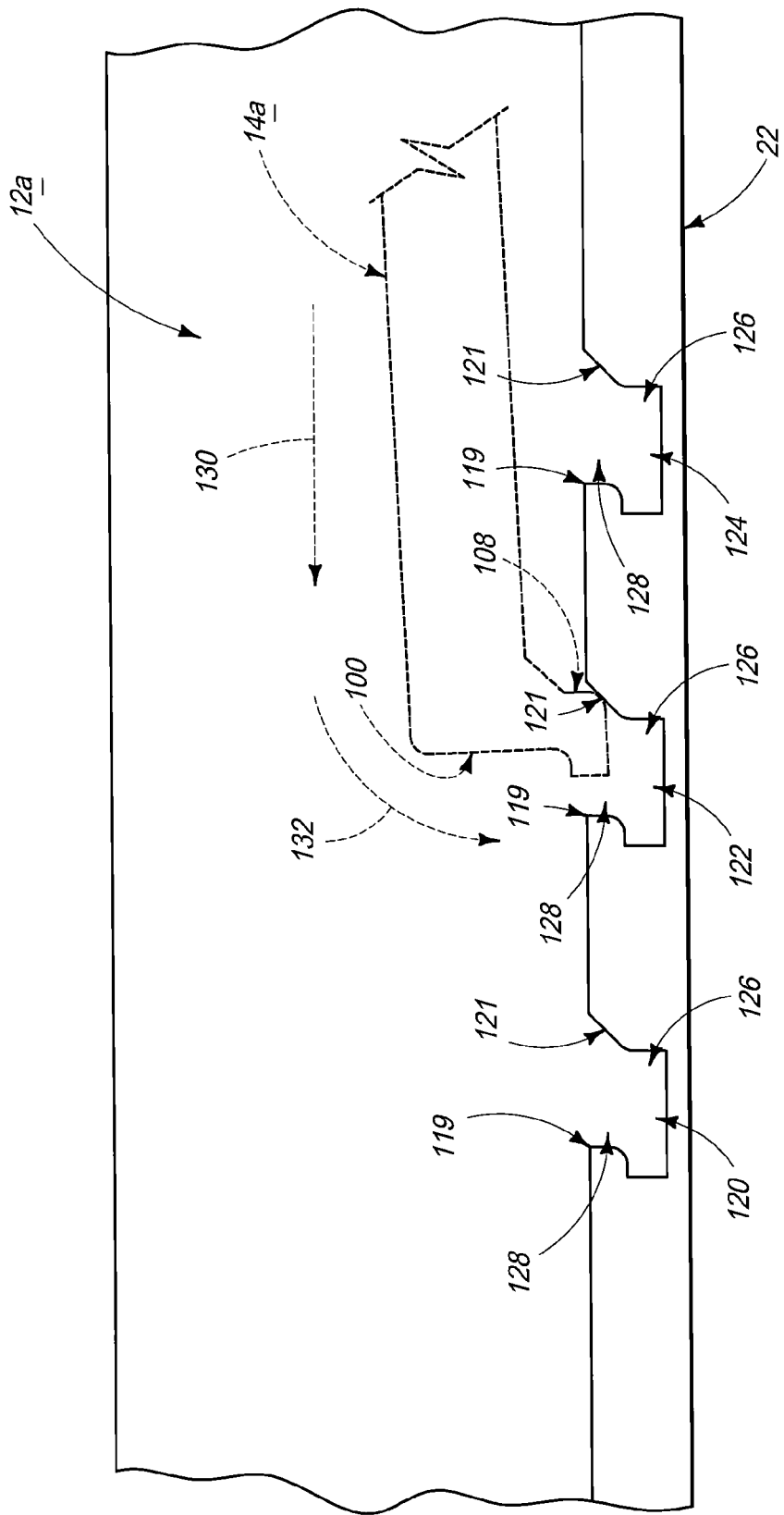
Figure 16:
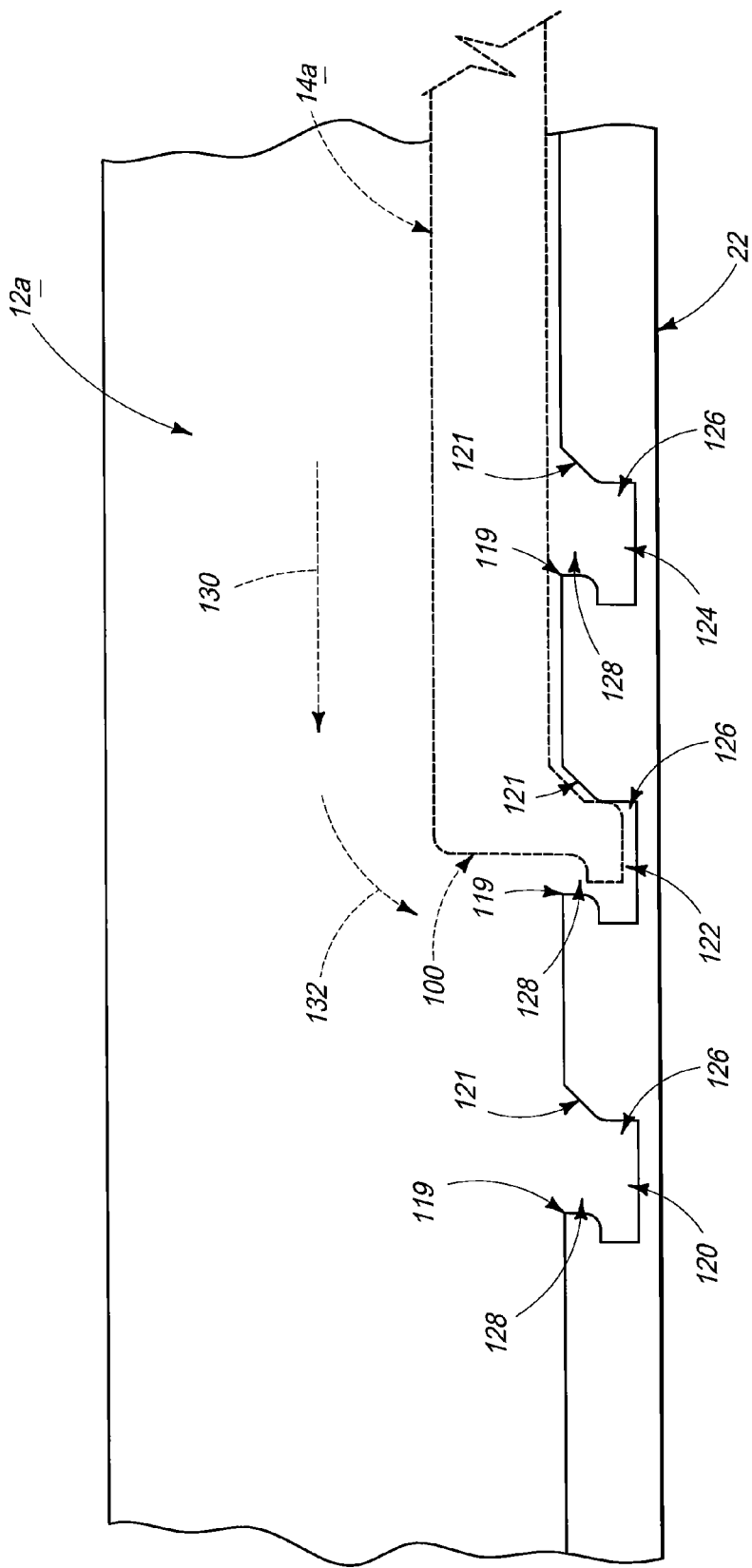

FIGS. 15 and 16 show the retaining structure 108 of deflectable region 100 falling into cavity 122 of bite block 12a. Directions of movement of region 100 are indicated by arrows 130 and 132.

Figure 17:
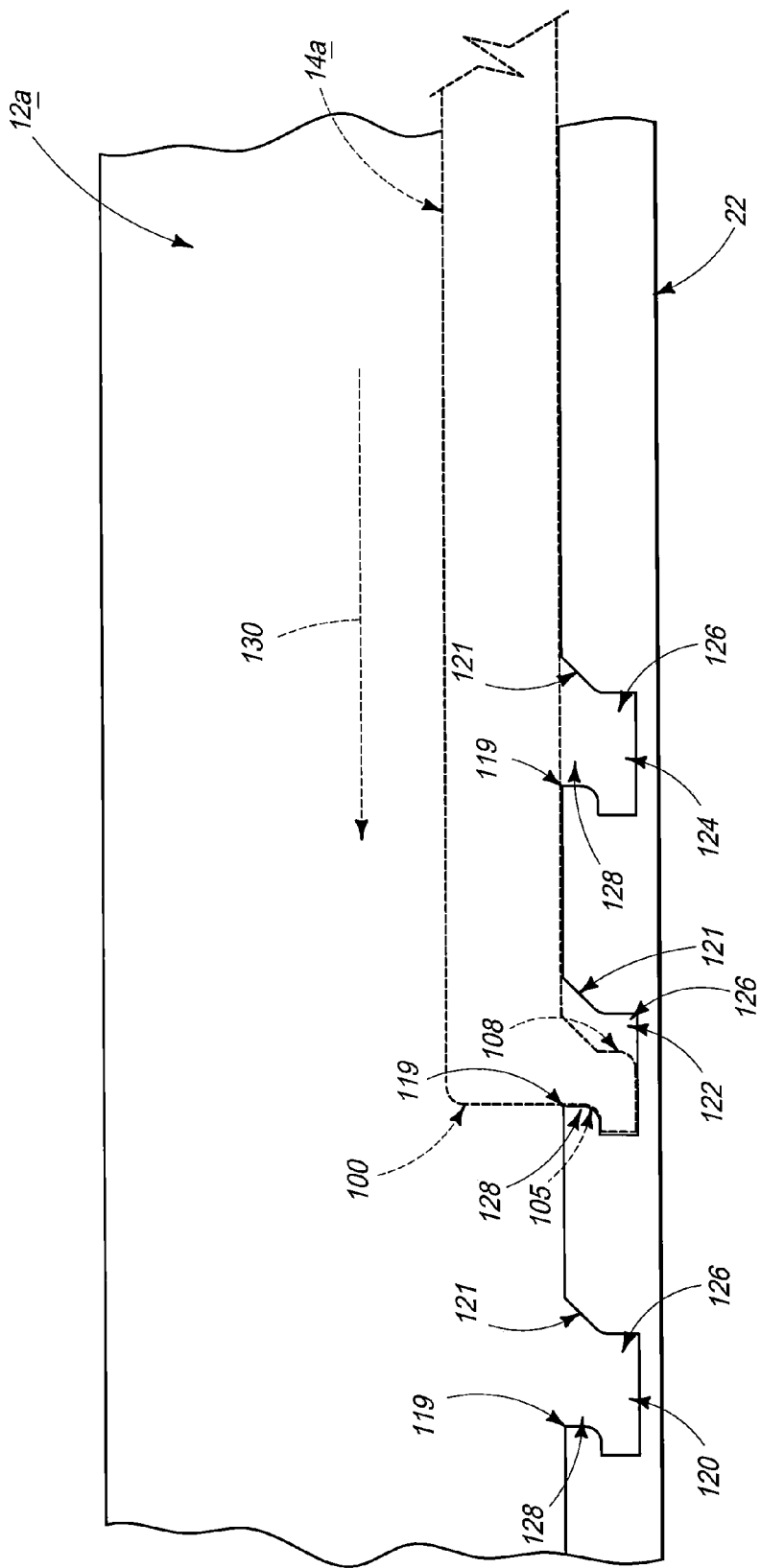

FIG. 17 shows the retaining structure 108 of deflectable region 100 locking into cavity 122. More specifically, the surface 105 of the deflectable region 100 engages with the ridge 119 of the "L"-shaped cavity and precludes further movement of tongue deflector 14a along the direction indicated by arrow 130.

It is noted that the retaining structure 108 may be removed from within the cavity by pulling deflectable region 100 in a direction opposite to the direction of arrow 130. Specifically, the sloped region 121 of the cavity, in combination with the sloped surface 109 of deflectable region 100, enables retaining structure 108 to be lifted out of the cavity when the deflectable region 100 is pulled in a direction opposite to arrow 130. Thus, deflectable region 100 locks securely into one of the cavities 120, 122 and 124 when pushed in the direction of arrow 130, and may be released from within the cavity when pulled in a direction opposite to arrow 130.

The direction of arrow 130 may be referred to as a downstream direction (and specifically, such direction would be in a direction down a patient's throat in an orientation in which an adjustable oral airway device is utilized), and the direction opposite to arrow 130 may then be referred to as an upstream direction. Accordingly, deflectable region 100 of tongue deflector 14a may be considered to slide into cavities 120, 122 and 124 to preclude movement of the tongue deflector in the downstream direction, while enabling movement in the upstream direction. In operation, a mask over a patient's mouth may provide pressure on a tongue deflector to press the tongue deflector in the downstream direction and keep it locked within one of the cavities 120, 122 and 124.

In some embodiments, an adjustable oral airway device utilizing tongue deflector 14a and bite block 12a may be provided so that the deflectable region 100 is locked in the furthest downstream cavity (for instance, cavity 120 of FIGS. 14-17). Then an operator of the device may simply slide the tongue deflector upstream if it is desired to adjust the tongue deflector.

Figure 18:
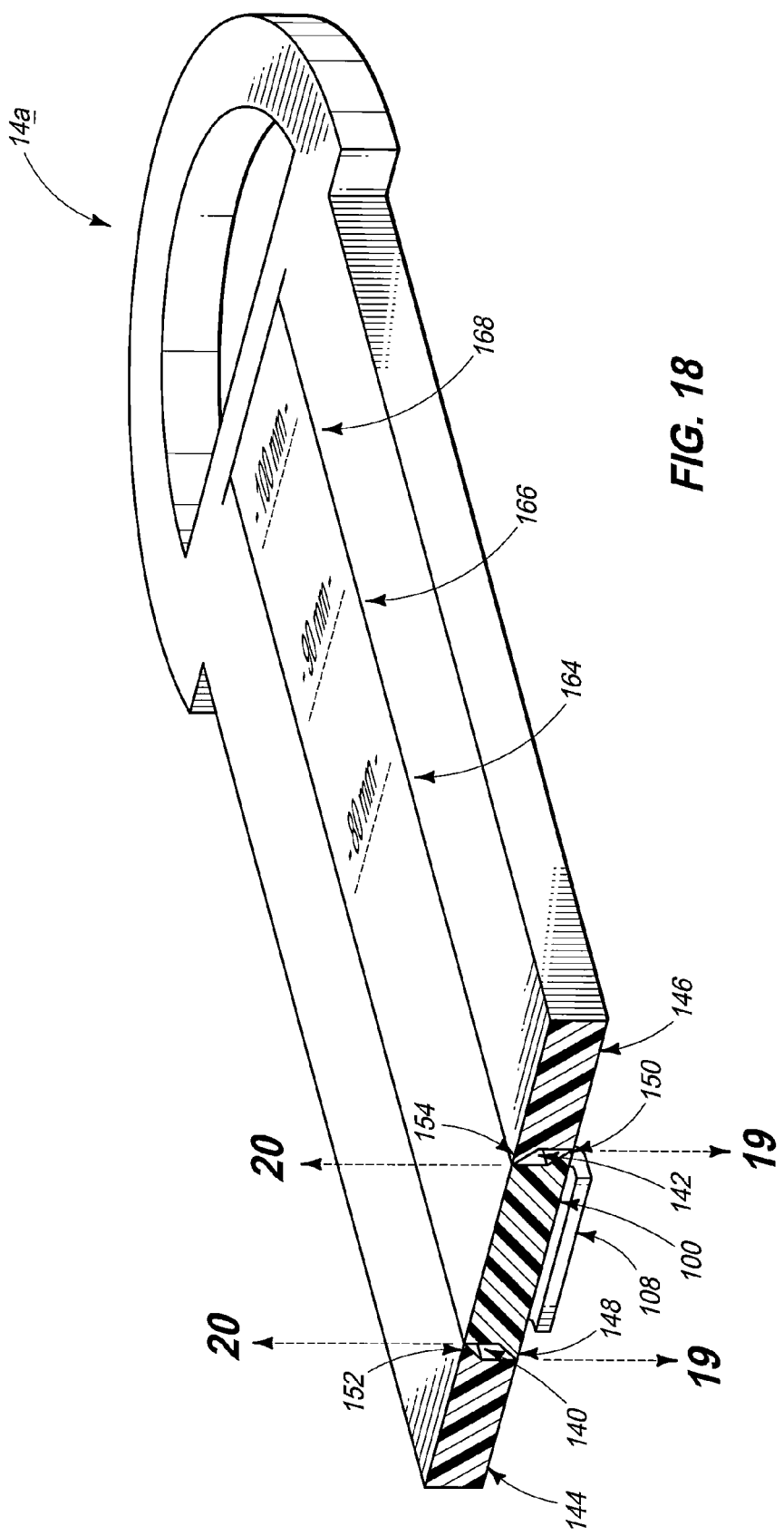
FIGS. 18-20 are views of the tongue deflector portion of FIG. 9 showing different stages of flexion of a biasing member of the tongue deflector portion. The views of FIGS. 18-20 are along a line labeled "18, 19, 20" of FIG. 9.
Figure 19:
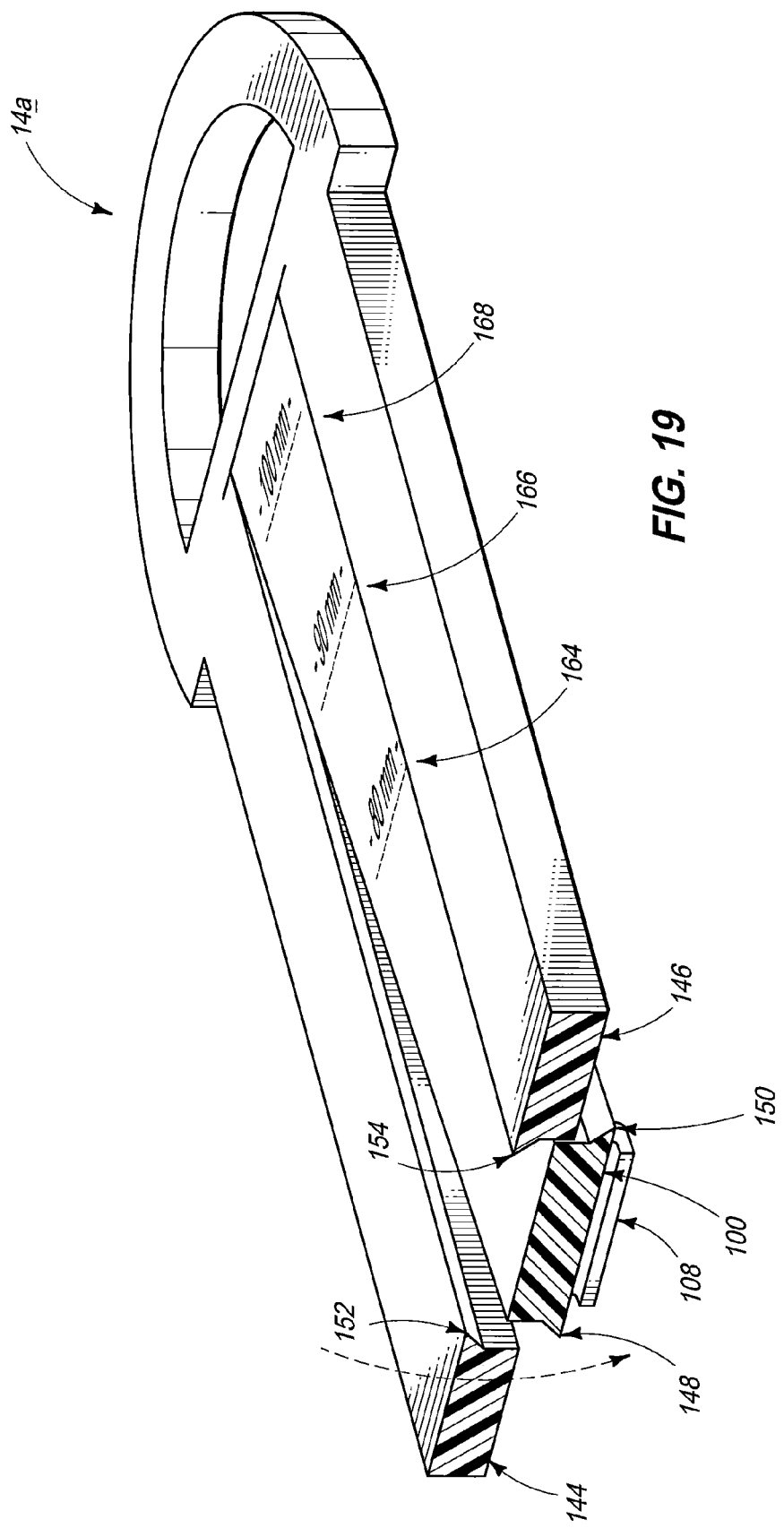
Figure 20:
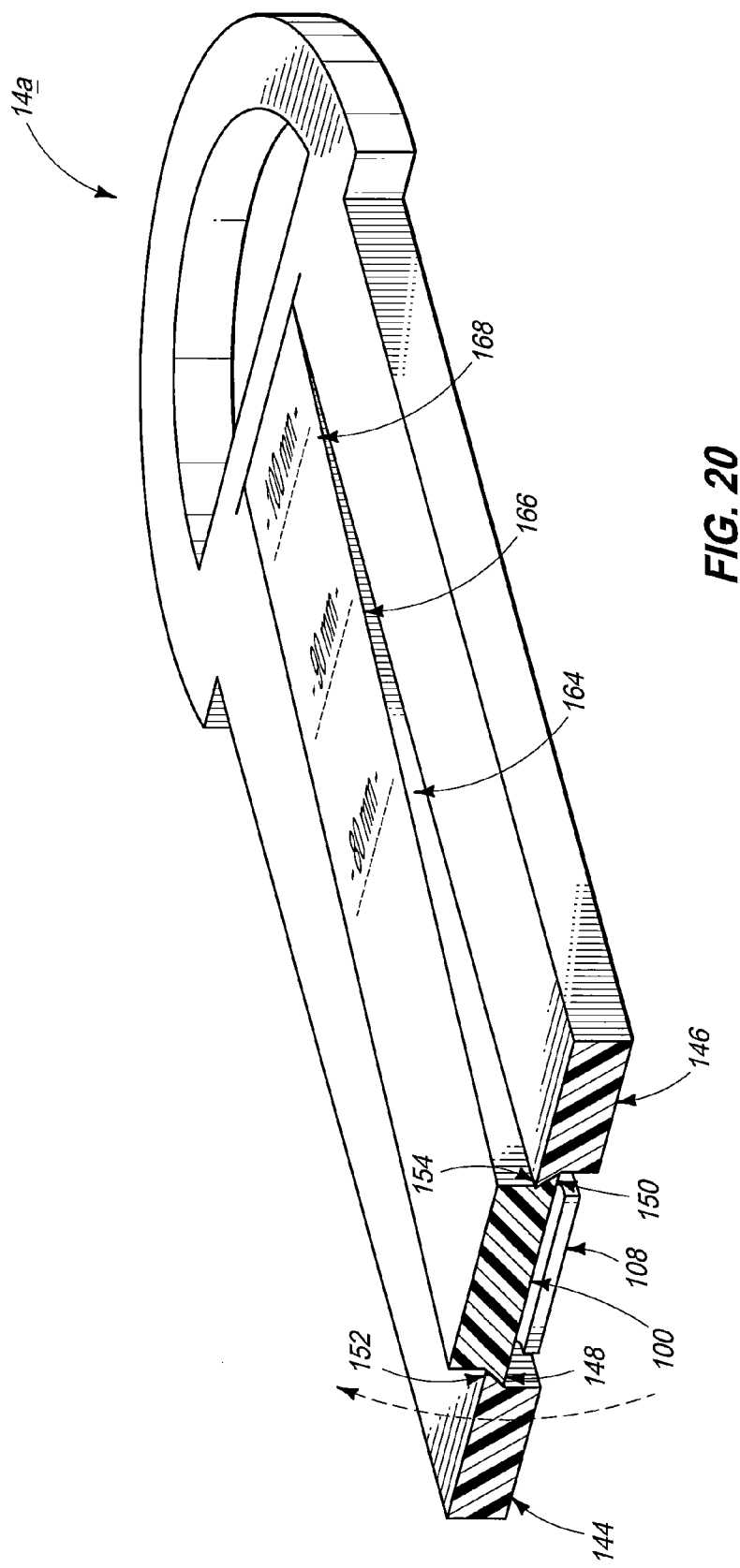

The deflectable region 100 has a bias that tends to push it into one of the cavities 120, 122 and 124 as the deflectable region passes across such cavity. The deflectable region may be passed over a cavity along the direction of arrow 130 if a counter-bias is provided to the deflectable region so that the deflectable region does not fall into the cavity. FIGS. 18-20 illustrate an embodiment in which an operator's fingers may be utilized to provide a counter-bias enabling the deflectable region to passed over cavities 120, 122 and 124 in the direction of arrow 130. FIGS. 18-20 show tongue deflector 14a with a cross sectional cut along an edge of deflectable region 100. Such cross sectional cut enables illustration of gaps 140 and 142 formed between lateral edges of the deflectable portion and adjacent edges of non-deflecting portions 144 and 146 of tongue deflector 14a. The gaps 140 and 142 result from removal of lateral sidewall regions of deflectable portion 100, and removal of lateral sidewall regions of non-deflecting portions 144 and 146. Remaining corners along the lateral edges of deflectable portion 100 form projecting points (or wings) 148 and 150, and similarly remaining corners along the lateral edges of non-deflecting portions 144 and 146 form projecting points (or wings) 152 and 154.

FIG. 19 shows deflectable region 100 biased to extend downwardly relative to non-deflecting portions 144 and 146. Such would lead to locking of deflectable region 100 into the cavities 120, 122 and 124 of FIGS. 14-17. Deflectable region 100 may have a natural downward bias induced by the combination of the choice of material of tongue deflector 14a and the shape of the deflectable region relative to the non-deflecting region. Alternatively, or additionally, a user of the tongue deflector may impart a downward bias on the deflectable region by utilizing finger pressure against such deflectable region.

FIG. 20 shows deflectable region 100 biased upwardly relative to non-deflecting portions 144 and 146. Such would enable the deflectable region to be passed across cavities 120, 122 and 124 of FIGS. 14-17 in the downstream direction of arrow 130. The user of the tongue deflector may impart the upward bias on the deflectable region by utilizing finger pressure against such deflectable region. In the shown embodiment, the points 148 and 150 of the deflectable region engage the points 152 and 154 of the non-deflecting portions to prevent the deflectable region from being popped up and over the non-deflecting portions. This may assist in alleviating problems that could occur during use of tongue deflector 14a that would render the tongue deflector inoperable. In some embodiments, points 148, 150, 152 and 154 may be omitted if it is found that there is little risk of problems occurring from users popping the deflectable region up and over the non-deflecting portions.

The tongue deflector 14a has markings 164, 166 and 168 similar to the markings 64, 66 and 68 discussed above with reference to FIGS. 4 and 5. Tongue deflector 14a is an example of an embodiment in which text is provided with the markings to indicate a depth to which a bottom end of the tongue deflector will extend into a patient's throat when such markings are aligned with a bite block.

Figure 21:
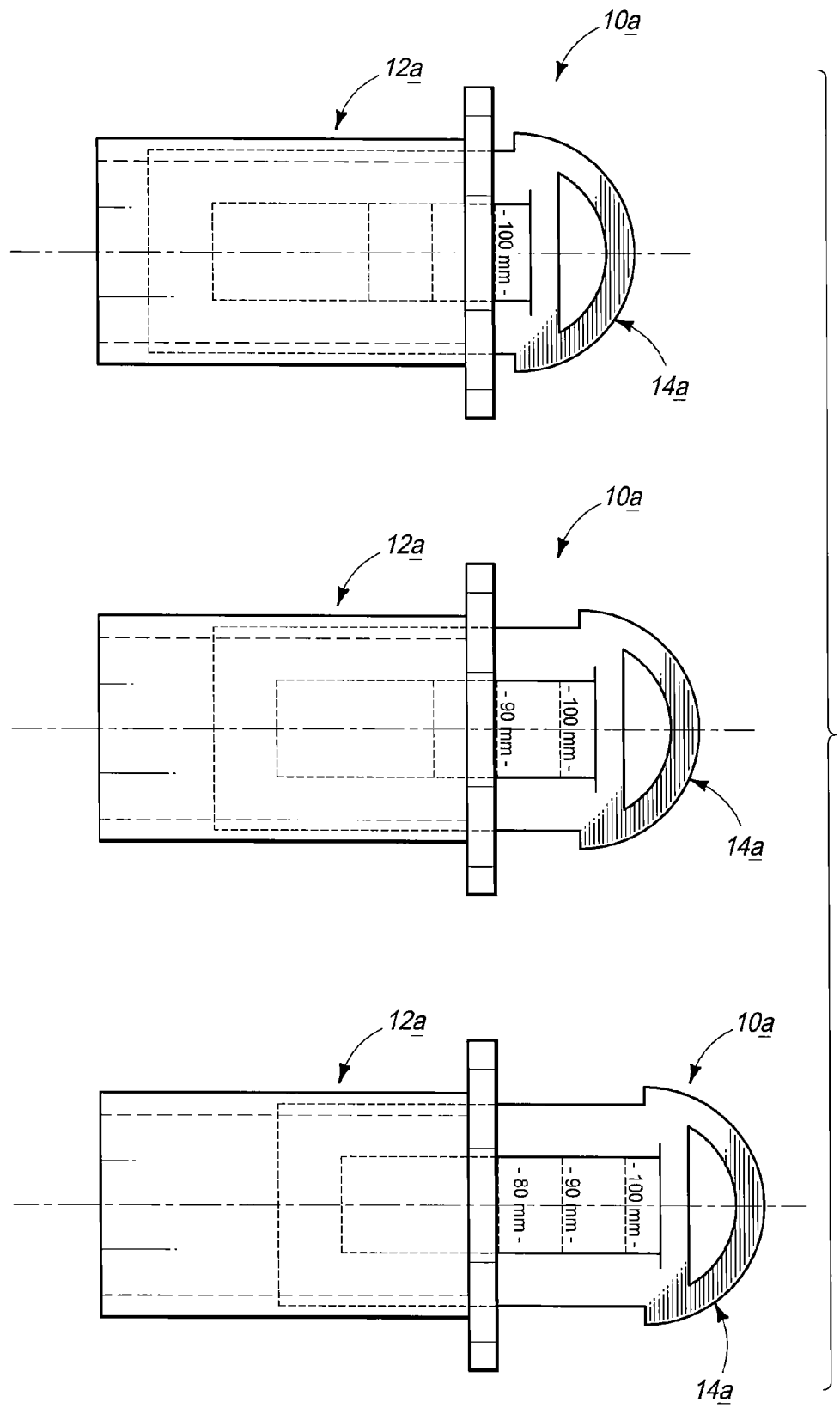
FIG. 21 shows top views of a portion of the example adjustable oral airway device of FIGS. 18-20 at three different size adjustments.

FIG. 21 shows an adjustable oral airway device 10a comprising the tongue deflector 14a in combination with the bite block 12a, and shows three specific predetermined positions that may be obtained by locking deflectable region 100 (FIGS. 14-17) into the various cavities 120, 122 and 124 (FIGS. 14-17).

In some embodiments, adjustable oral airway devices may be configured to be retained on a patient's head with a headband or other suitable structure. FIG. 22 shows bite block 12, and a portion of a headband 200. The bite block comprises the receptacles 202 and 204. The receptacles each have a wide region 204 joining to a narrow slot region 206. The headband 200 has a pin 210 attached thereto. The pin has a narrow stem region 212 extending to a wide head region 214.

In operation, the wide head region 214 of stem 212 may be passed through the wide region 204 of receptacle 200, and then the stem 212 may be slid down into the narrow region 206 of the receptacle. Once the stem is slid down into the narrow region 206, the stem becomes locked in the receptacle due to the head 214 being too wide to pass out of the narrow region 206. The shown method of attachment of the headband to the bite block 12 may be accomplished quickly in an emergency situation.

The pin 210 may be connected to the headband with any suitable means. FIGS. 23 and 24 illustrate one embodiment for attaching the pin to the headband. FIG. 23 shows a headband 200 having a pair of opposing ends 250 and 252. Each of the ends has an outer region 251 and an inner region 253, with the outer and inner regions being complementary parts of a hook and loop (e.g. VELCRO™) system. Thus, the outer regions may be folded onto the inner regions, and will then connect with the inner regions through the hook and loop attachment system.

FIG. 24 shows pins 210 joined on ends 250 and 252 by passing the ends of the headband through slots adjacent the pins (such slots are not visible in FIG. 24, but an example slot may be seen in FIG. 22 as a slot 260), and then folding the outer regions 251 onto the inner regions 253 to connect the outer regions to the inner regions and thereby retain the pins 210 to the headband 200. Such attachment may render the sizing of the headband to be adjustable by simply disconnecting the outer regions 251 from the inner regions 253, changing the amount of overlap of the outer regions over the inner regions, and then reattaching the outer regions to the inner regions.

Figure 25:
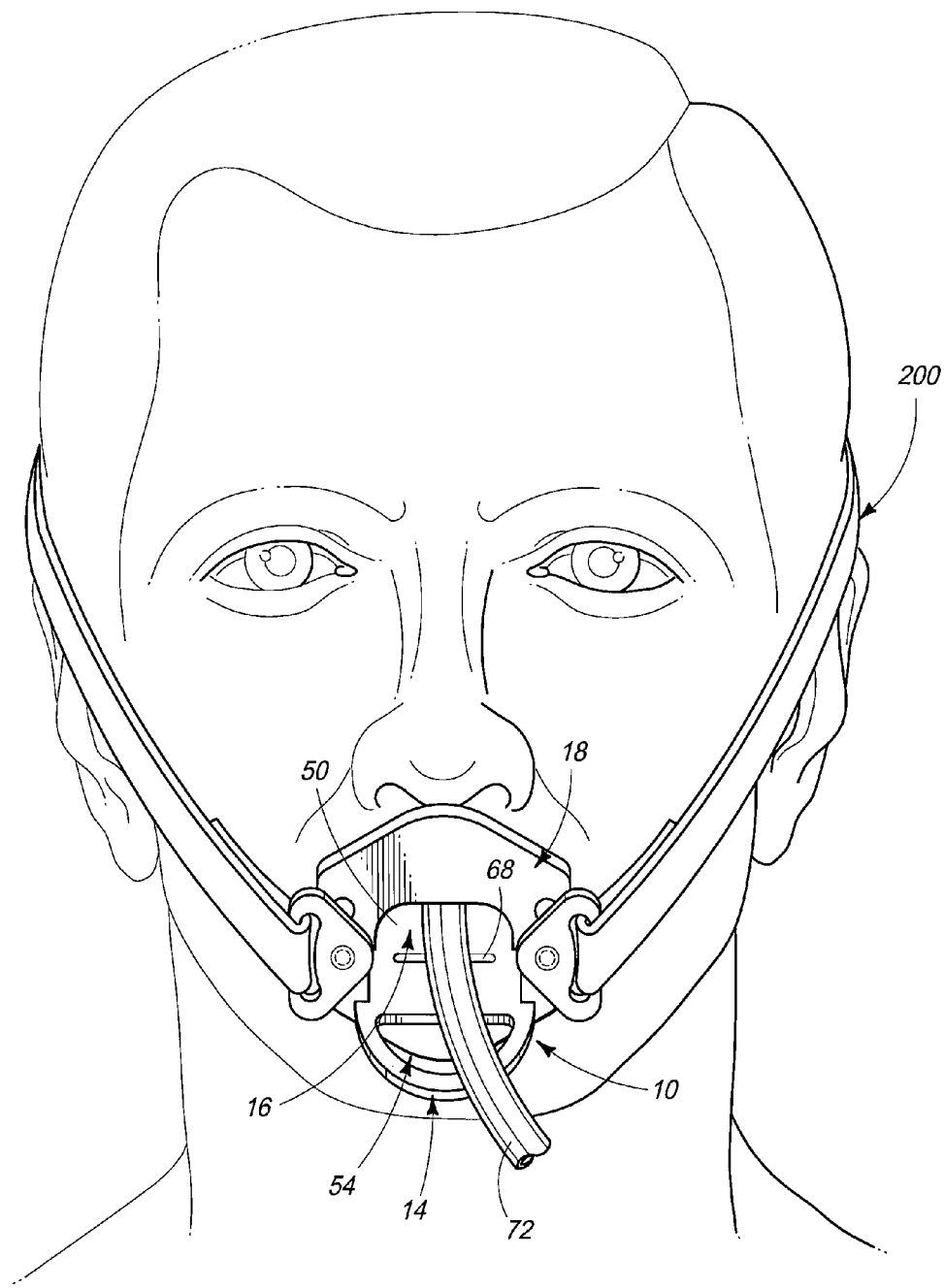
FIG. 25 shows an adjustable oral airway device retained to a person's head with a headband.

FIG. 25 shows an adjustable oral airway device 10 retained on a patient's mouth with a headband 200. A cannula 72 extends into the opening 16 through the adjustable oral airway device. The tongue deflector 14 also extends within the opening 16, and the cannula is along an upper surface of the tongue deflector. The shown tongue deflector has a loop 54 to enable grasping by an operator, and has a marking 68 to provide a visual reference to the operator of how deep the end of the deflector is in the patient's mouth. A mask (not shown) may be provided over the patient's mouth and nose, and over the adjustable oral airway device, to assist in providing ventilation for the patient.

The various manipulations of the tongue deflector (for instance, movement of the tongue deflector within the bite block for sizing of the adjustable oral airway devices, removal of the tongue deflector from the bite block if a patient regains consciousness and becomes uncomfortable with the tongue deflector in his mouth, etc.) may be accomplished with limited manual dexterity, and thus may be accomplished with gloves on and/or with a loss of a fine motor skills that may occur in a stressful situation.

The adjustable oral airway devices shown herein may be particularly advantageous for utilization by professional medical emergency response personnel, in that the adjustable oral airway devices can take up less room in a toolbox than a large number of differently sized oral airway devices, and can be rapidly deployed under adverse and stressful conditions. However, the adjustable oral airway devices are not limited to emergency response applications, and may also be utilized in other applications in which breathing assistance may be administered, such as, for example, in hospitals (or other medical facilities) when patients are anesthetized during surgery.

Figure 26:
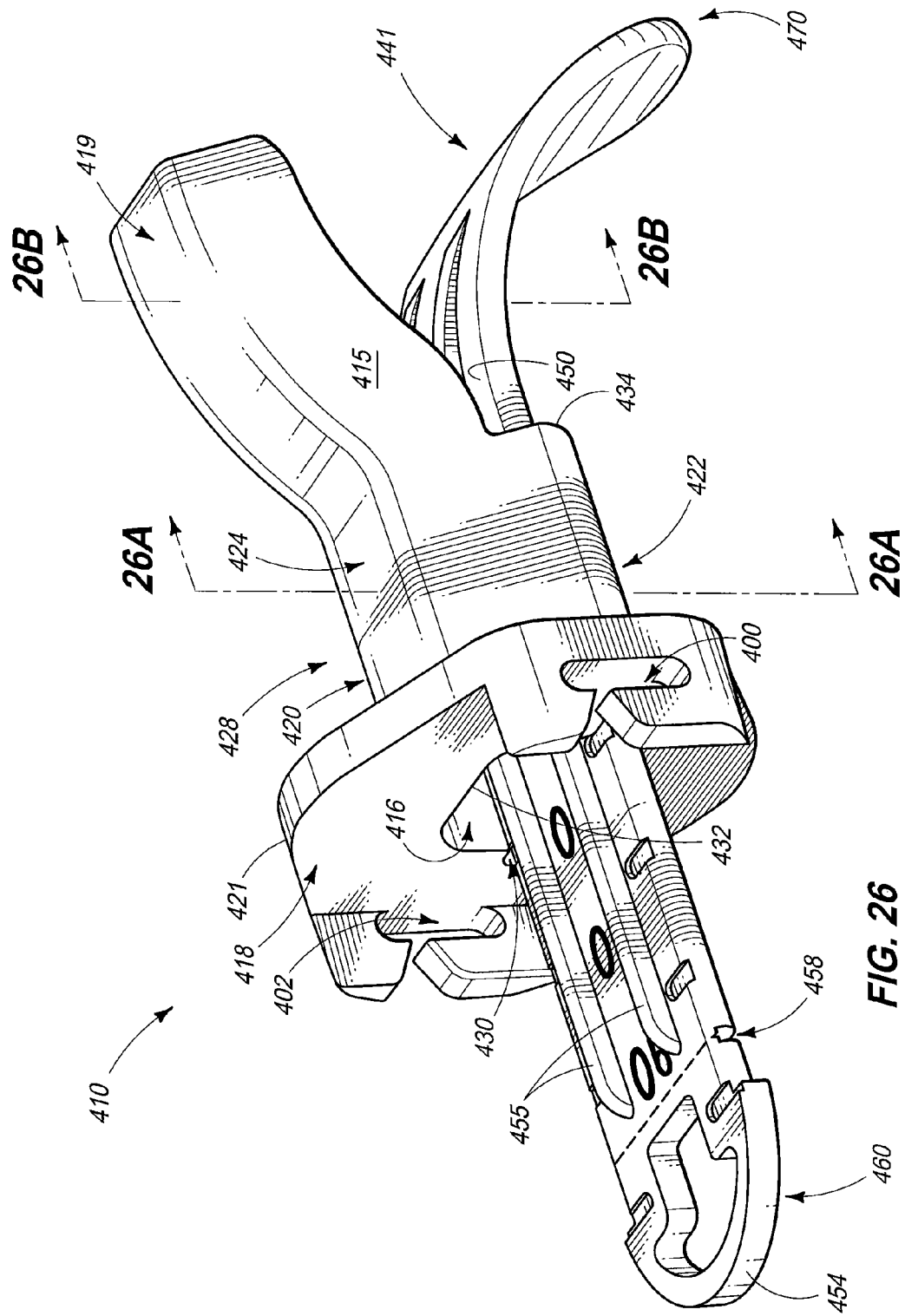
FIG. 26 is a three-dimensional view of an example adjustable oral airway assembly according to an embodiment.

According to additional embodiments, oral assemblies are described with reference to FIGS. 26 through 34. Referring first to FIG. 26, an oral assembly 410 is provided that includes a body 428 having an opening 416 extending from a first end 432 of body 428 to a second end 434. Body 428 can be fabricated according to the materials and/or methods described herein. Body 428 can have upper portion 420 and lower portion 422 in one cross section. Assembly 410 can also include a flange 421 extending from first end 432 of body 428 outwardly from opening 416. Protruding at opposing edges of flange 421 can be loops 400 and 402. As shown, loops 400 and 402 can be partial loops or claws, for example. These loops can extend normally from surface 418 of flange 421, for example.

Assembly 410 can also include an upper member 415 that extends from upper portion 420. Member 415 can include sidewalls as shown, for example. When in engaged orally, body 428 may be engaged by the lips or teeth of the patient. In this engagement, member 415 may engage the palate of the mouth.

Assembly 410 further includes a lower member 450 slidably engaged with body 428. According to certain implementations, at least a portion 441 of lower member 450 extends outwardly from lower portion 422 of second end 434 of body 428 and away from upper potion 420 when engaged with body 428. When engaged orally, as described herein, member 450 can engage the tongue of the patient. In accordance with example implementations, where member 415 engages the palate of the patient and member 450 engages the tongue of the patient, an airway can be provided within the patient's mouth. Both the palate and tongue of the patient when engaged with assembly 410 in this fashion can stabilize assembly 410 within the mouth.

Referring to FIG. 26A, a cross-section of assembly 410 is provided. Referring to FIG. 26A, body 428 can include a substantially planar base 426 having a pair of opposing sidewalls 418 extending to a top 424. In accordance with example implementations, each of opposing sidewalls 418 may be configured to curve outwardly away from base 426, then over base 426 to form a slot 430 (shown in FIGS. 26, 27, and 28, for example) above base 426. Slot 430 can be configured to slidably engage lower member 450. As can be seen in FIG. 26A, at least a portion of each of opposing sidewalls 418 can extend inwardly over base 426 to top 424. In accordance with example implementations, at least a portion of top 424 is substantially planar. Base 426 can be substantially wider than top 424 in one cross section, for example. In accordance with an example embodiment, where at least a portion of top 424 is substantially planar, upper portion 420 of body 428 can form a chute 417.

Referring next to FIG. 26B, another cross section of assembly 410 is provided. In accordance with this cross section, chute 417 is comprised by upper member 415. Chute 417 can extend upwardly from second end 434 of body 428 and outwardly from opening 416 to form a platform 419 spaced elevationally away from top 424 of body 428 in one cross section (see FIG. 28A for example). In accordance with example implementations, chute 417 can engage the palate as well as portion of the upper jaw when engaged orally by a patient. Chute 417 can further stabilize assembly 410 within the mouth of the patient.

Referring next to FIG. 27, and in accordance with example implementations, assembly 410 is shown with body 428 separated from lower member 450. End 470 of lower member 450 can be inserted into slot 430 of opening 416 within body 428. Member 450 can slidably engage body 428, for example.

Referring next to FIGS. 28 and 28A, a front view of body 428 is shown in FIG. 28. As can be seen from this front view, opening 416 includes a slot 430 as described. Within body 428, a notch 436 can be provided. Notch 436 can be configured to receive a portion of member 450, for example. Referring to FIG. 28A, body 428 can include edges 432 defining opening 416. Flange 421 can include a planar surface 418 extending normally from edges 432 of opening 416, for example. In accordance with example implementations, at least one of the edges is substantially planar. In accordance with example implementations, body 428 can include edges 435 of opening 416, which can include a beveled portion between the planar edge of opening 416 and planar surface 418 of flange 421. Edge 435 can be utilized as a ramp to receive member 450, for example. According to example implementations, notch 436 can be formed within planar edge 435.

Figure 29:
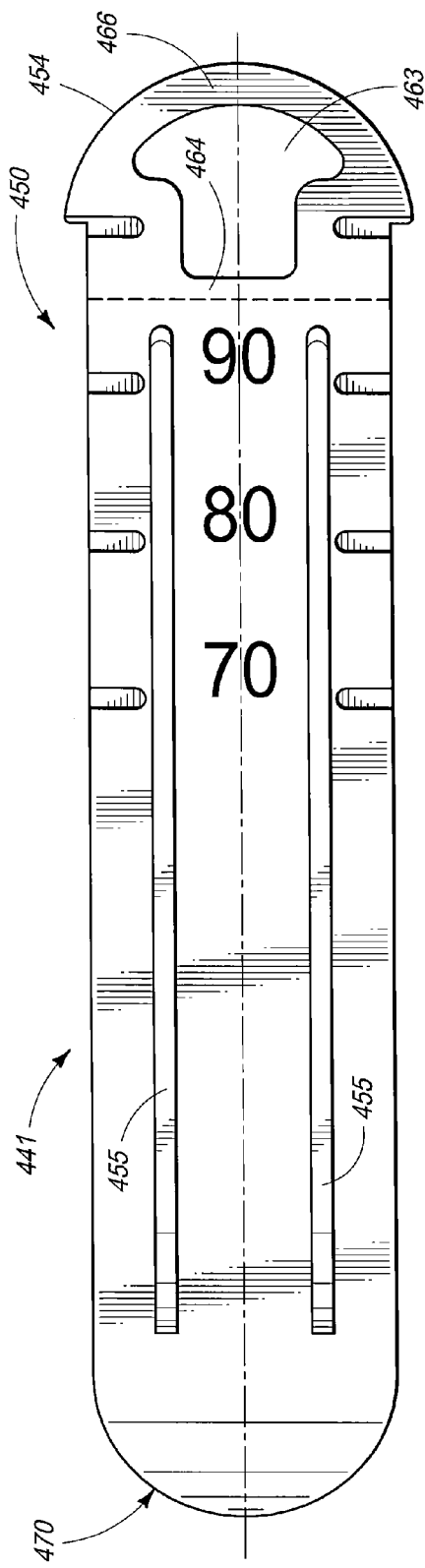
FIG. 29 is a view of an elevation of another component of the assembly of FIG. 26.
Figure 30:
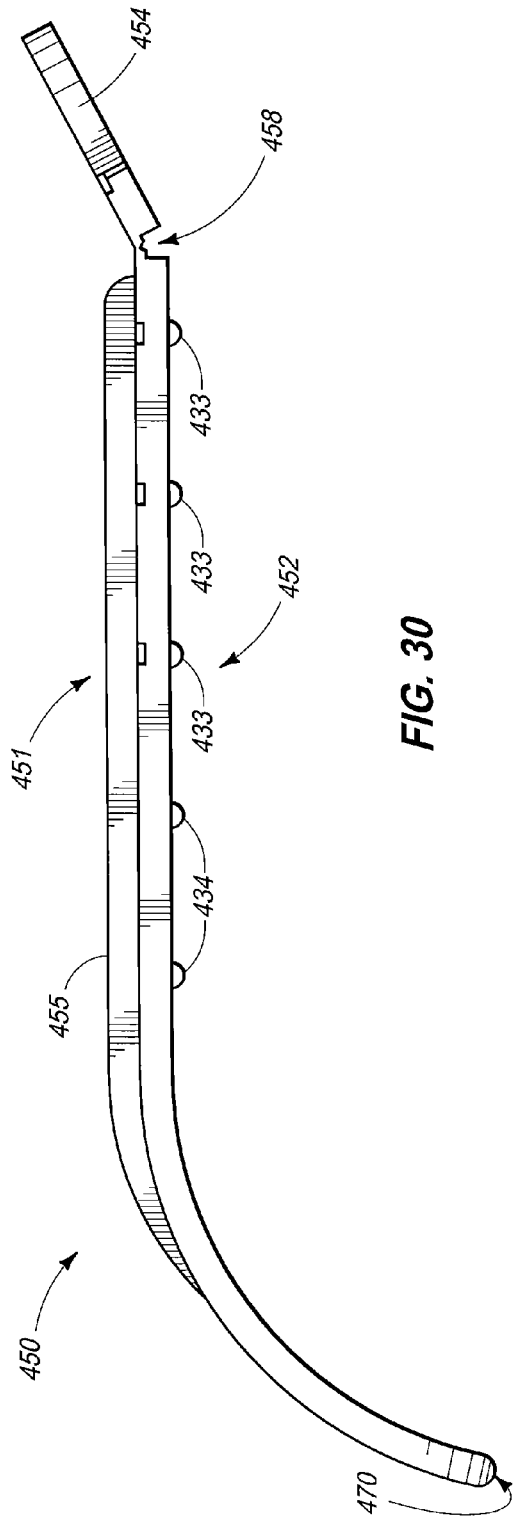
FIG. 30 is a view of another elevation of the other component of the assembly of FIG. 26.

Referring to FIGS. 29 and 30, member 450 can include an upper side 451 and a lower side 452. Lower side 452 can comprise a plurality of projections 433. In accordance with example implementations, these projections can be aligned longitudinally along lower side 452 of member 450. Projections 433 can be in pairs 434. These pairs can be equivalently spaced apart. Projections 433 can be configured to be engaged by notch 436 for example. According to an example implementation, member 450 may further include a pair of rails 455 along upper side 451. These rails can extend longitudinally the length of at least a portion of member 450. Rails 455 may be utilized to guide additional apparatus in the mouth, such as evacuation tubes for example. Member 450 can include a tab 454. Tab 454 can include a framed opening 463 defined by a base 464 extending to a substantially arcuate terminus 466.

Figure 31:
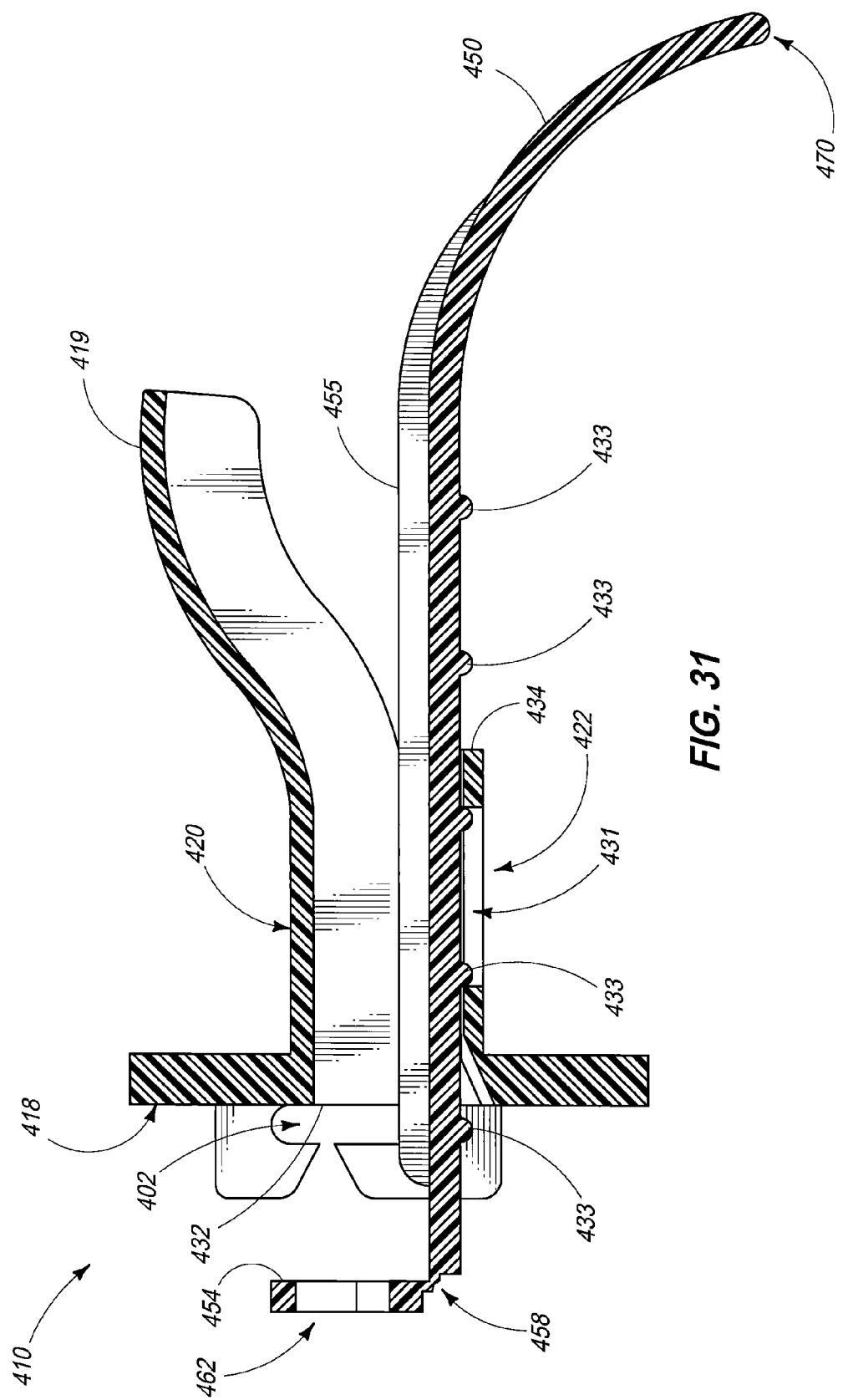
FIG. 31 is another cross section view of the airway assembly of FIG. 26.

Referring next to FIG. 31, tab 454 can be pivotally coupled to member 450. The pivotal coupling can include providing a recess 458 between tab 454 and member 450 to rely on the resiliency of the polymer-based member to allow for pivoting between at least two positions relative to one another. As shown in FIG. 31, tab 454 is shown in position normal to the member 450. Referring to FIGS. 26 and 31, for example, tab 454 can be configured to pivot between a first position as shown in FIG. 26 aligned with member 450 and a second position as shown in FIG. 31 normal to member 450. In accordance with example implementations, in this position assembly 410 may be utilized in combination with a breathing mask for example. The positioning of the tab 454 normal to member 450 can provide space to allow the proper coupling of the breathing mask to the patient.

Figure 31A:
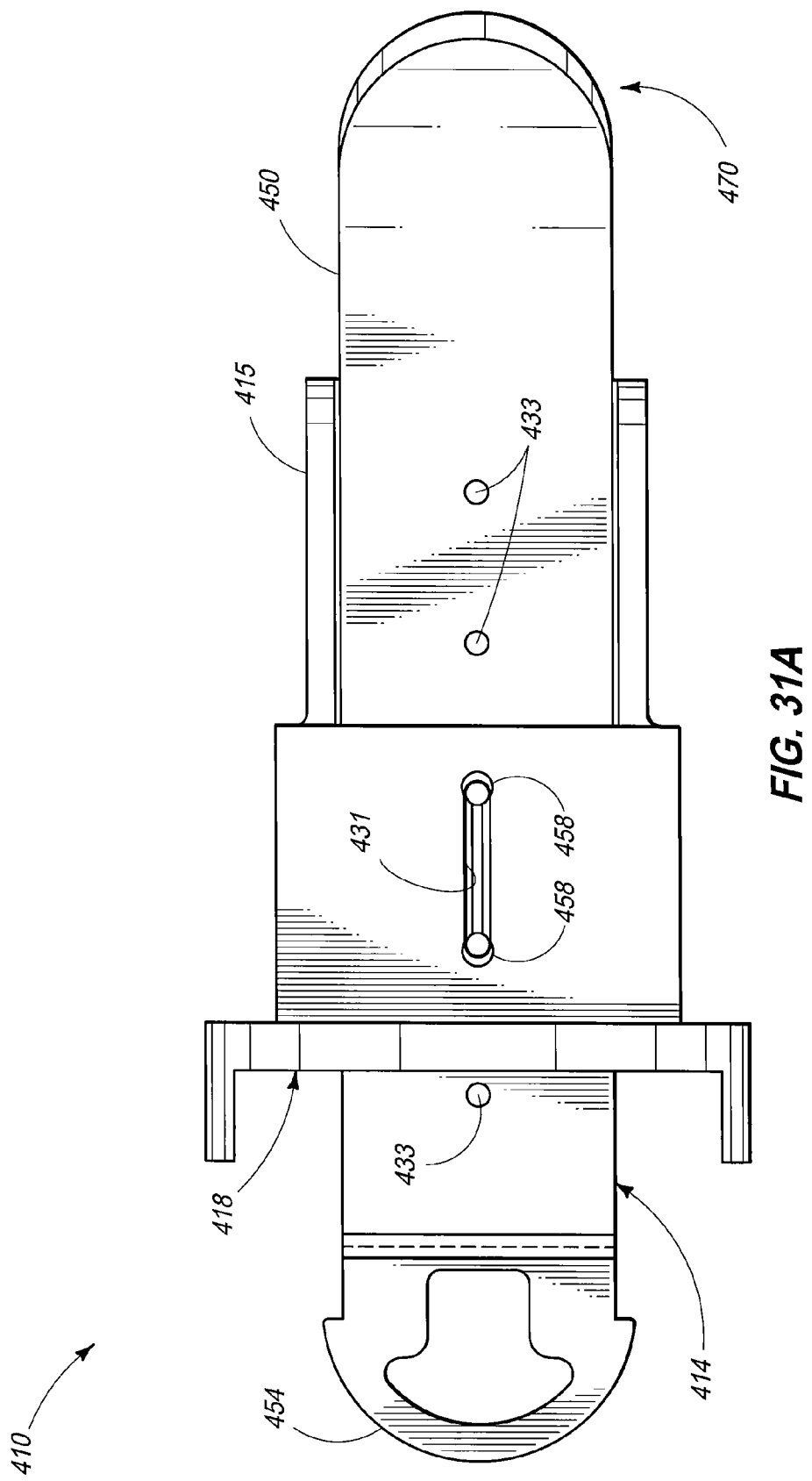
FIG. 31A is a view of another elevation of the airway assembly of FIG. 26.

Referring next to FIG. 31A, a view of the lower side of body 428 is shown. In accordance with example embodiments, body 428 can define a slot 431 aligned longitudinally along lower portion 422 of body 428. Body 428 can further define notches 458 at opposing ends of slot 431. Each of notches 458 can be configured to receive at least one of the pair 434 of projections 433 of lower member 450, for example. In accordance with example configurations, a distance between notches 458 can be equivalent to the distance between projections 433 of pair 434. The location of notches 458 along lower portion 422 of body 428 in combination with the location of pairs 434 along lower side 452 of member 450 can selectively place member 450 in relation to body 428. For example, demarcations along member 450 can indicate the depth to which member 450 extends from second end 434 of body 428. The engagement of pairs 434 with notches 458 can align these demarcations along first end 432 of body 428, for example.

Figure 32:
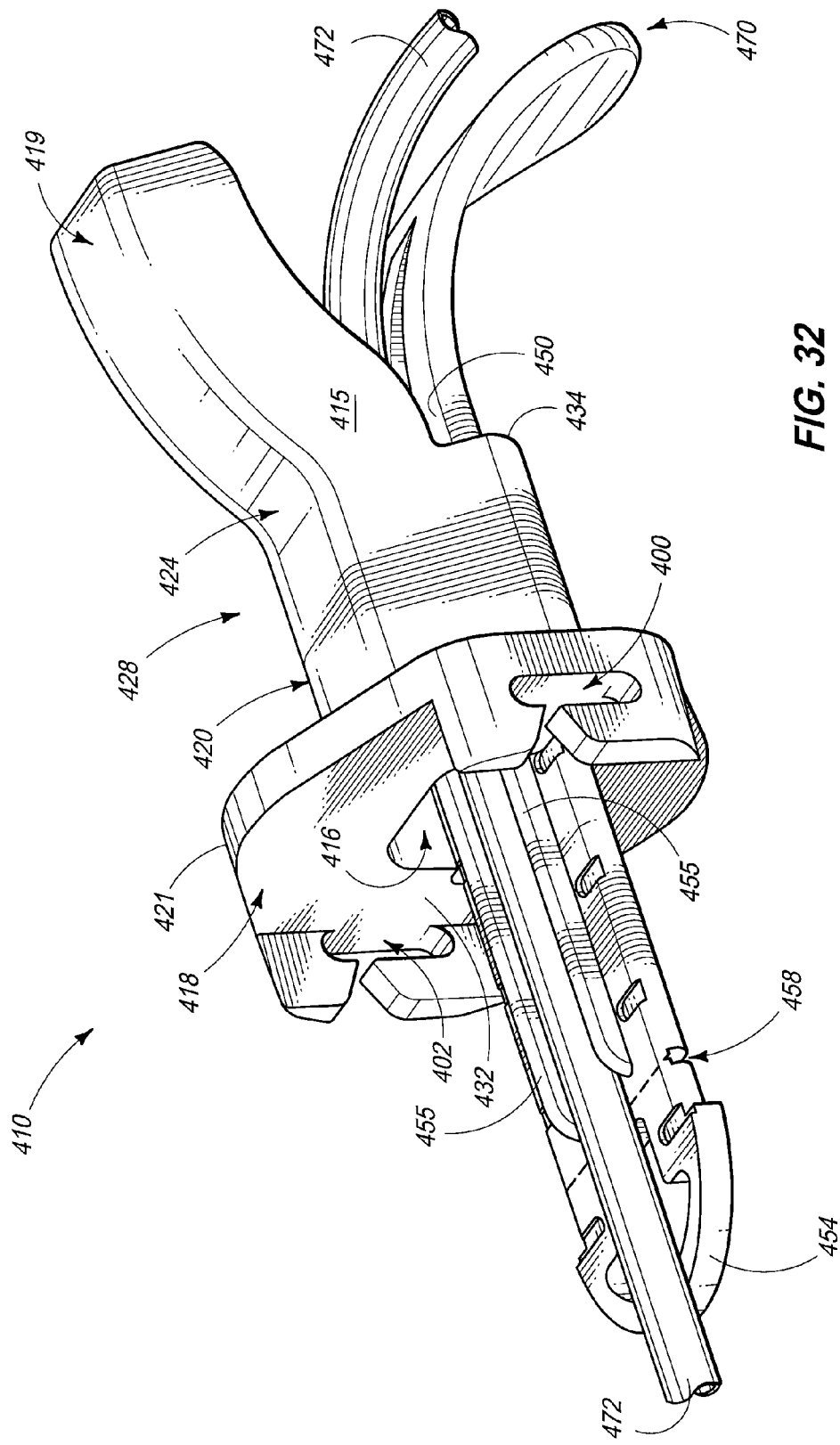
FIG. 32 is a three dimensional view of the assembly of FIG. 26 in one configuration.
Figure 33:
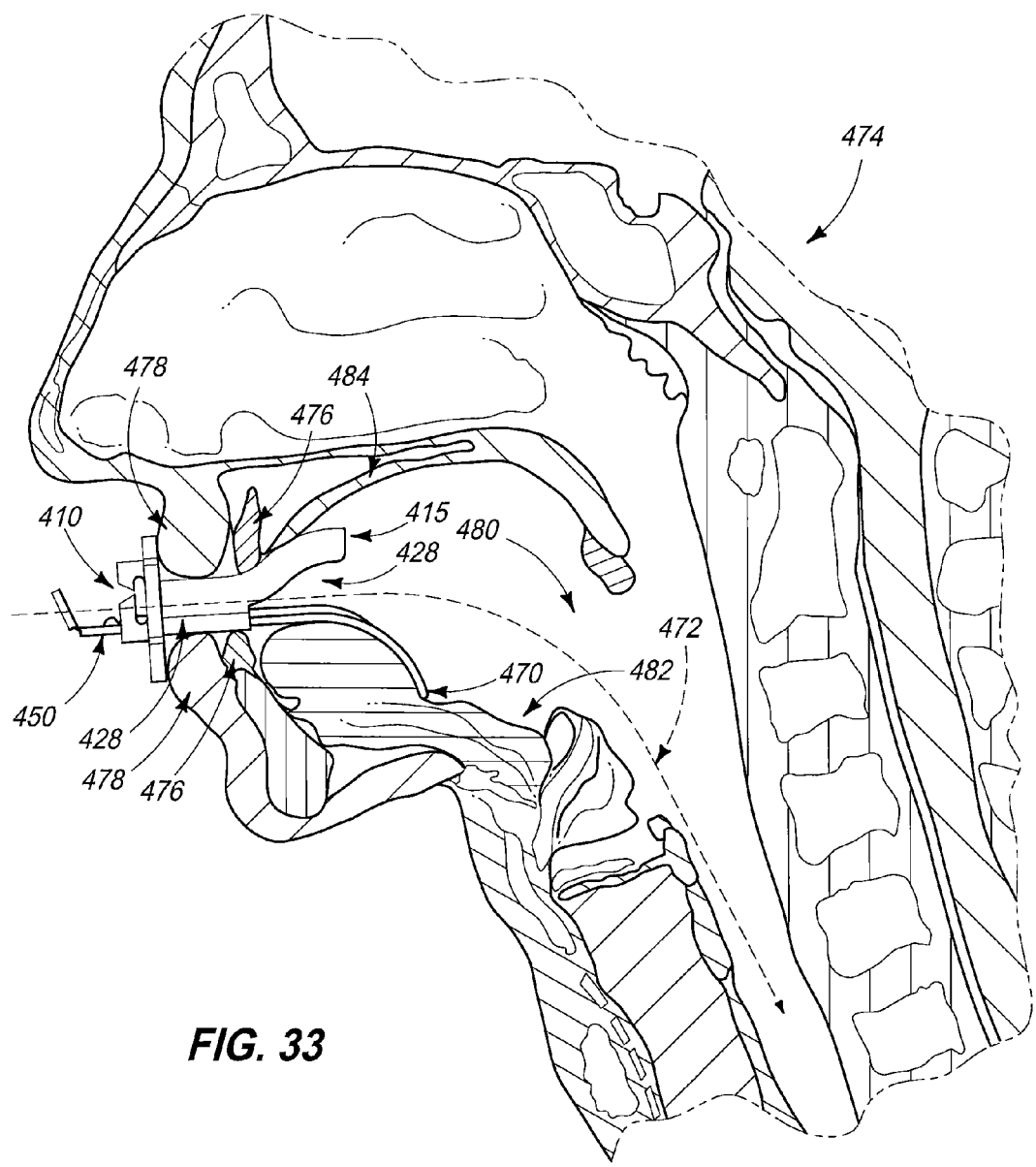
FIG. 33 is a view of the assembly of FIG. 26 engaged orally.
Figure 34:
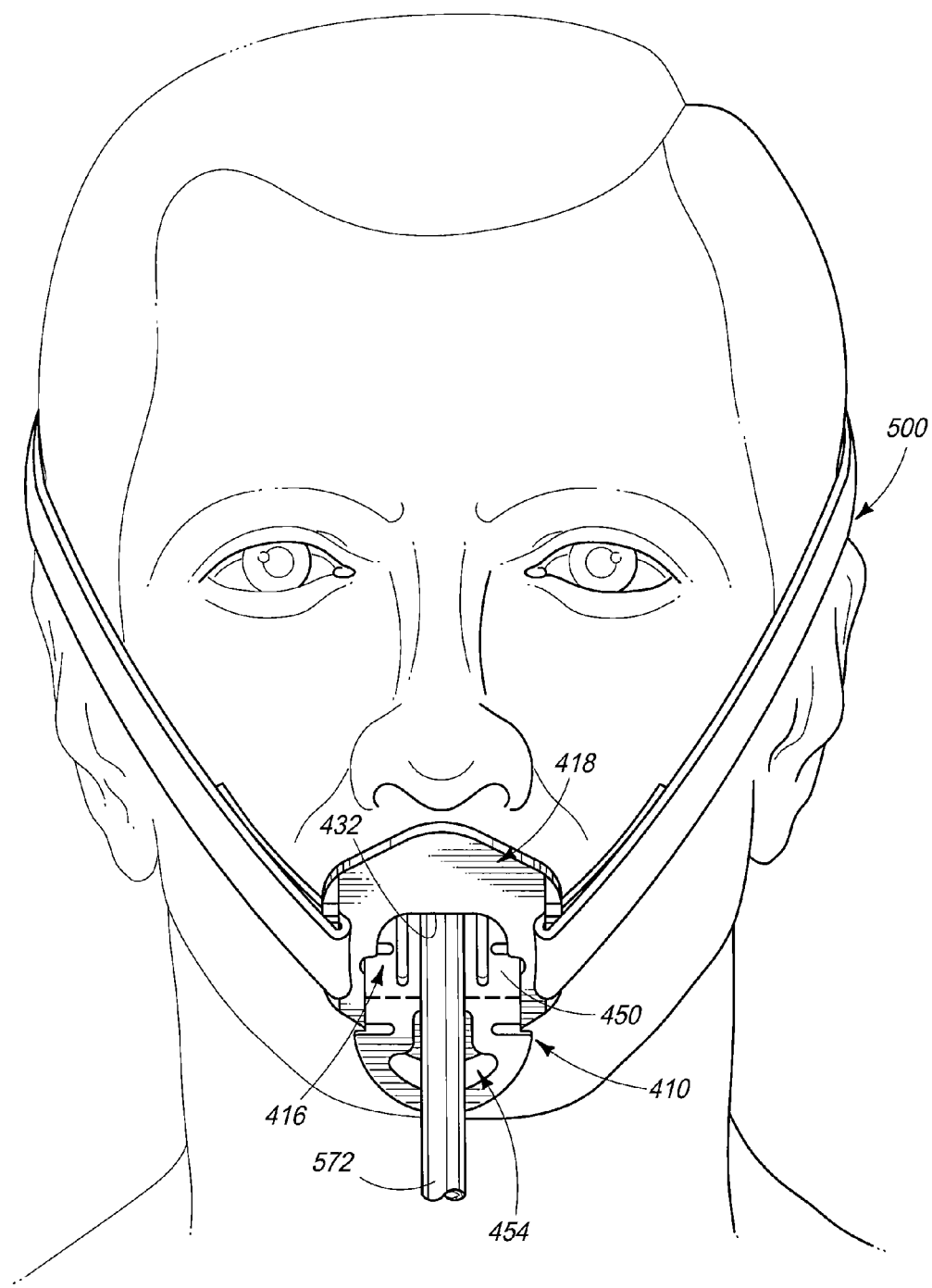
FIG. 34 is a front elevation of the assembly of FIG. 26 engaged orally.

Referring to FIGS. 32-34, assembly 410 is shown in combination with other apparatus as well as engaged orally. Vacuum tube 472 is shown operatively engaged with assembly 410. In this configuration tube 472 resides between rails 455 of member 450. Further, tab 454 is in the planar position rather than the normal position. When engaged by a patient as shown in FIGS. 33 and 34, member 450 can engage tongue 482 while member 415 engages palate 484. As shown in FIG. 34, straps 500 secure assembly 410 to the patient by adjustably connecting to loops 402 and 400, for example.

In compliance with the statute, the subject matter disclosed herein has been described in language more or less specific as to structural and methodical features. It is to be understood, however, that the claims are not limited to the specific features shown and described, since the means herein disclosed comprise example embodiments. The claims are thus to be afforded full scope as literally worded, and to be appropriately interpreted in accordance with the doctrine of equivalents.

We claim:

1. An oral airway assembly comprising:
   a tubular body extending from a first end of the body to a second end of the body, the body having upper and lower portions in one cross section;
   a flange extending outwardly from the first end of the body;
   an upper chute member extending from the upper portion of the second end of the body and outwardly from the body away from the lower portion;
   a lower member slidably engaged through the tubular body, at least a portion of the lower member extending outwardly from the lower portion of the second end of the body and away from the upper chute when engaged with the body;
   wherein the body comprises a substantially planar base having a pair of opposing sidewalls extending to a top in the one cross section such that the body defines an opening; and
   wherein each of the opposing sidewalls curve outwardly away from the base then over the base to form a slot above the base, the slot being located within the opening and configured to receive the lower member.

2. The oral airway assembly of claim 1 wherein at least a portion of each of the opposing sidewalls extend inwardly over the base to the top.

3. The oral airway assembly of claim 2 wherein at least a portion of the top is substantially planar, the base being substantially wider than the top in the one cross section.

4. The oral airway assembly of claim 2 wherein at least a portion of the top is substantially planar, the upper portion of the body defining the chute.

5. The oral airway assembly of claim 4 wherein the chute extends upwardly from the second end of the body and outwardly from the opening to form a platform spaced elevationally away from the top of the body.

6. The oral airway assembly of claim 1 wherein the first end of the body comprises edges defining the opening, the flange including a planar surface extending normally from the edges of the opening, wherein at least one of the edges is substantially planar.

7. The oral airway assembly of claim 6 further comprising a beveled portion between the planar edge of the opening and the planar surface of the flange.

8. The oral airway assembly of claim 6 further comprising a notch within the planar edge, the notch configured to receive a portion of the lower member.

\* \* \* \* \*

UNITED STATES PATENT AND TRADEMARK OFFICE
CERTIFICATE OF CORRECTION

PATENT NO. : 8,931,477 B2
APPLICATION NO. : 13/023873
DATED : January 13, 2015
INVENTOR(S) : Daniel Ogilvie and Beata Zawadzka Page 1 of 1

It is certified that error appears in the above-identified patent and that said Letters Patent is hereby corrected as shown below:

In the specification,

Column 1, line 48 – Replace "response personal" with --response personnel--

Column 3, line 34 – Replace "may utilized" with --may be utilized--

Column 12, line 3 – Replace "when in engaged" with --when engaged--

Column 12, line 11 – Replace "upper potion" with --upper portion--

Signed and Sealed this
Seventeenth Day of May, 2016

Michelle K. Lee
*Director of the United States Patent and Trademark Office*